(12) United States Patent
Barry et al.

(10) Patent No.: US 8,734,380 B2
(45) Date of Patent: May 27, 2014

(54) DETERMINING PATIENT-SPECIFIC VAPOR TREATMENT AND DELIVERY PARAMETERS

(71) Applicant: Uptake Medical Corp., Tustin, CA (US)

(72) Inventors: Robert L. Barry, Kirkland, WA (US); Brian Cran, Seattle, WA (US); Erik Henne, Seattle, WA (US); Daniel Reddy, Seattle, WA (US); Dean Corcoran, Bothell, WA (US)

(73) Assignee: Uptake Medical Corp., Tustin, CA (US)

( * ) Notice: Subject to any disclaimer, the term of this patent is extended or adjusted under 35 U.S.C. 154(b) by 0 days.

(21) Appl. No.: 13/675,989

(22) Filed: Nov. 13, 2012

(65) Prior Publication Data

US 2013/0211393 A1 Aug. 15, 2013

Related U.S. Application Data

(63) Continuation of application No. 12/409,370, filed on Mar. 23, 2009, now Pat. No. 8,322,335, which is a continuation-in-part of application No. 12/256,197, filed on Oct. 22, 2008, now Pat. No. 8,147,532.

(60) Provisional application No. 61/038,718, filed on Mar. 21, 2008, provisional application No. 60/981,701, filed on Oct. 22, 2007.

(51) Int. Cl.
*A61B 18/04* (2006.01)
*A61B 18/00* (2006.01)

(52) U.S. Cl.
CPC ....... *A61B 18/04* (2013.01); *A61B 2018/00625* (2013.01); *A61B 2018/00577* (2013.01)
USPC .............................. 604/23; 606/21; 607/113

(58) Field of Classification Search
CPC ..................... A61B 2018/00625; A61B 18/04; A61B 2018/048; A61B 2018/00577; A61B 17/12022; A61K 2300/00
USPC .................. 128/898; 604/19–21, 23, 28, 500; 606/20–23, 27, 28; 607/96, 104, 105, 607/107, 113
See application file for complete search history.

(56) References Cited

U.S. PATENT DOCUMENTS

| 3,880,168 A | 4/1975 | Berman |
| 4,773,410 A | 9/1988 | Blackmer et al. |

(Continued)

FOREIGN PATENT DOCUMENTS

| AU | 721086 B2 | 6/2000 |
| EP | 1003582 B1 | 2/2003 |

(Continued)

OTHER PUBLICATIONS

Becker, et al.; Lung volumes before and after lung volume reduction surgery; Am J Respir Crit Care Med; vol. 157; pp. 1593-1599; (1998) Oct. 28, 1997.

(Continued)

*Primary Examiner* — Nicholas Lucchesi
*Assistant Examiner* — Gerald Landry, II
(74) *Attorney, Agent, or Firm* — Shay Glenn LLP

(57) ABSTRACT

Methods and systems for determining patient specific treatment parameters for delivering vapor to the lung to treat lung tissue. In some embodiments vapor is delivered to the lung to cause coagulative necrosis, inducing fibrosis and thereby reducing the volume of at least one segment of the lung. The delivery parameters can be adjusted depending on the desired degree of injury to be induced in the lung tissue.

10 Claims, 17 Drawing Sheets

(56) References Cited

U.S. PATENT DOCUMENTS

| | | | |
|---|---|---|---|
| 4,793,352 A | 12/1988 | Eichenlaub | |
| 4,915,113 A | 4/1990 | Holman | |
| 4,950,266 A | 8/1990 | Sinofsky | |
| 5,006,119 A | 4/1991 | Acker et al. | |
| 5,011,566 A | 4/1991 | Hoffman | |
| 5,084,043 A | 1/1992 | Hertzmann et al. | |
| 5,112,328 A | 5/1992 | Taboada et al. | |
| 5,158,536 A | 10/1992 | Sekins et al. | |
| 5,263,951 A | 11/1993 | Spears et al. | |
| 5,331,947 A | 7/1994 | Shturman | |
| 5,334,190 A | 8/1994 | Seiler | |
| 5,348,551 A | 9/1994 | Spears et al. | |
| 5,352,512 A | 10/1994 | Hoffman | |
| 5,424,620 A | 6/1995 | Cheon et al. | |
| 5,462,521 A | 10/1995 | Brucker et al. | |
| 5,500,012 A | 3/1996 | Brucker et al. | |
| 5,503,638 A | 4/1996 | Cooper et al. | |
| 5,524,620 A | 6/1996 | Rosenschein | |
| 5,529,076 A | 6/1996 | Schachar | |
| 5,549,628 A | 8/1996 | Cooper et al. | |
| 5,562,608 A * | 10/1996 | Sekins et al. | 604/20 |
| 5,575,803 A | 11/1996 | Cooper et al. | |
| 5,591,157 A | 1/1997 | Hennings et al. | |
| 5,620,440 A | 4/1997 | Heckele et al. | |
| 5,695,507 A | 12/1997 | Auth et al. | |
| 5,735,811 A | 4/1998 | Brisken | |
| 5,752,965 A | 5/1998 | Francis et al. | |
| 5,755,753 A | 5/1998 | Knowlton | |
| 5,782,914 A | 7/1998 | Schankereli | |
| 5,800,482 A | 9/1998 | Pomeranz et al. | |
| 5,824,703 A | 10/1998 | Clark, Jr. | |
| 5,827,268 A | 10/1998 | Laufer | |
| 5,913,856 A | 6/1999 | Chia et al. | |
| 5,957,919 A | 9/1999 | Laufer | |
| 5,964,752 A | 10/1999 | Stone | |
| 5,972,026 A | 10/1999 | Laufer et al. | |
| 5,986,662 A | 11/1999 | Argiro et al. | |
| 5,989,445 A | 11/1999 | Wise et al. | |
| 6,032,077 A | 2/2000 | Pomeranz | |
| 6,053,909 A | 4/2000 | Shadduck | |
| 6,059,011 A | 5/2000 | Giolo | |
| 6,083,255 A | 7/2000 | Laufer et al. | |
| 6,099,251 A | 8/2000 | LaFleur | |
| 6,102,037 A | 8/2000 | Koch | |
| 6,113,722 A | 9/2000 | Hoffman et al. | |
| 6,130,671 A | 10/2000 | Argiro | |
| 6,139,571 A | 10/2000 | Fuller et al. | |
| 6,162,232 A | 12/2000 | Shadduck | |
| 6,194,066 B1 | 2/2001 | Hoffman | |
| 6,200,333 B1 | 3/2001 | Laufer | |
| 6,210,404 B1 | 4/2001 | Shadduck | |
| 6,219,059 B1 | 4/2001 | Argiro | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,299,633 B1 | 10/2001 | Laufer | |
| 6,300,150 B1 | 10/2001 | Venkatasubramanian | |
| 6,312,474 B1 | 11/2001 | Francis et al. | |
| 6,327,505 B1 | 12/2001 | Medhkour et al. | |
| 6,394,949 B1 | 5/2002 | Crowley et al. | |
| 6,398,775 B1 | 6/2002 | Perkins et al. | |
| 6,409,723 B1 | 6/2002 | Edwards | |
| 6,411,852 B1 | 6/2002 | Danek et al. | |
| 6,458,231 B1 | 10/2002 | Wapner et al. | |
| 6,468,313 B1 | 10/2002 | Claeson et al. | |
| 6,488,673 B1 | 12/2002 | Laufer et al. | |
| 6,493,589 B1 | 12/2002 | Medhkour et al. | |
| 6,508,816 B2 | 1/2003 | Shadduck | |
| 6,527,761 B1 | 3/2003 | Soltesz et al. | |
| 6,585,639 B1 | 7/2003 | Kotmel et al. | |
| 6,588,613 B1 | 7/2003 | Pechenik et al. | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,629,951 B2 | 10/2003 | Laufer et al. | |
| 6,652,594 B2 | 11/2003 | Francis et al. | |
| 6,653,525 B2 | 11/2003 | Ingenito et al. | |
| 6,669,694 B2 | 12/2003 | Shadduck | |
| 6,679,264 B1 | 1/2004 | Deem et al. | |
| 6,682,520 B2 | 1/2004 | Ingenito | |
| 6,692,494 B1 | 2/2004 | Cooper et al. | |
| 6,712,812 B2 | 3/2004 | Roschak et al. | |
| 6,719,738 B2 | 4/2004 | Mehier | |
| 6,755,794 B2 | 6/2004 | Soukup | |
| 6,770,070 B1 | 8/2004 | Balbierz | |
| 6,776,765 B2 | 8/2004 | Soukup et al. | |
| 6,860,847 B2 | 3/2005 | Alferness et al. | |
| 6,885,888 B2 | 4/2005 | Rezai | |
| 6,901,927 B2 | 6/2005 | Deem et al. | |
| 6,904,909 B2 | 6/2005 | Andreas et al. | |
| 6,907,881 B2 | 6/2005 | Suki et al. | |
| 6,911,028 B2 | 6/2005 | Shadduck | |
| 6,986,769 B2 | 1/2006 | Nelson et al. | |
| 6,997,189 B2 | 2/2006 | Biggs et al. | |
| 7,022,088 B2 | 4/2006 | Keast et al. | |
| 7,027,869 B2 | 4/2006 | Danek et al. | |
| 7,031,504 B1 | 4/2006 | Argiro et al. | |
| 7,083,612 B2 | 8/2006 | Littrup et al. | |
| 7,128,748 B2 | 10/2006 | Mooradian et al. | |
| 7,136,064 B2 | 11/2006 | Zuiderveld | |
| 7,144,402 B2 | 12/2006 | Kuester, III | |
| 7,144,588 B2 | 12/2006 | Oray et al. | |
| 7,175,644 B2 | 2/2007 | Cooper et al. | |
| 7,192,400 B2 | 3/2007 | Campbell et al. | |
| 7,198,635 B2 | 4/2007 | Danek et al. | |
| 7,233,820 B2 | 6/2007 | Gilboa | |
| 7,235,070 B2 | 6/2007 | Vanney | |
| 7,335,195 B2 | 2/2008 | Mehier | |
| 7,347,859 B2 | 3/2008 | Garabedian et al. | |
| 7,412,977 B2 | 8/2008 | Fields et al. | |
| 7,422,563 B2 | 9/2008 | Roschak et al. | |
| 7,422,584 B2 | 9/2008 | Loomas et al. | |
| 7,425,212 B1 | 9/2008 | Danek et al. | |
| 7,462,162 B2 | 12/2008 | Phan et al. | |
| 7,517,320 B2 | 4/2009 | Wibowo et al. | |
| 7,708,712 B2 | 5/2010 | Phan et al. | |
| 7,740,017 B2 | 6/2010 | Danek et al. | |
| 7,778,704 B2 | 8/2010 | Rezai | |
| 7,815,590 B2 | 10/2010 | Cooper | |
| 7,819,908 B2 | 10/2010 | Ingenito | |
| 7,906,124 B2 | 3/2011 | Laufer et al. | |
| 7,913,698 B2 | 3/2011 | Barry et al. | |
| 7,993,323 B2 | 8/2011 | Barry et al. | |
| 8,002,740 B2 | 8/2011 | Willink et al. | |
| 8,088,127 B2 | 1/2012 | Mayse et al. | |
| 8,172,827 B2 | 5/2012 | Deem et al. | |
| 8,251,070 B2 | 8/2012 | Danek et al. | |
| 8,292,882 B2 | 10/2012 | Danek et al. | |
| 8,322,335 B2 | 12/2012 | Barry et al. | |
| 2002/0077516 A1 | 6/2002 | Flanigan | |
| 2002/0111386 A1 | 8/2002 | Sekins et al. | |
| 2002/0177846 A1 * | 11/2002 | Mulier et al. | 606/27 |
| 2003/0099279 A1 | 5/2003 | Venkatasubramanian et al. | |
| 2003/0181922 A1 | 9/2003 | Alferness | |
| 2003/0228344 A1 * | 12/2003 | Fields et al. | 424/423 |
| 2004/0031494 A1 | 2/2004 | Danek et al. | |
| 2004/0038868 A1 | 2/2004 | Ingenito | |
| 2004/0047855 A1 | 3/2004 | Ingenito | |
| 2004/0055606 A1 | 3/2004 | Hendricksen et al. | |
| 2004/0068306 A1 * | 4/2004 | Shadduck | 607/96 |
| 2004/0199226 A1 | 10/2004 | Shadduck | |
| 2004/0244803 A1 | 12/2004 | Tanaka | |
| 2005/0016530 A1 | 1/2005 | McCutcheon et al. | |
| 2005/0166925 A1 | 8/2005 | Wilson et al. | |
| 2005/0171396 A1 | 8/2005 | Pankratov et al. | |
| 2005/0171582 A1 | 8/2005 | Matlock | |
| 2005/0203483 A1 | 9/2005 | Perkins et al. | |
| 2005/0215991 A1 | 9/2005 | Altman et al. | |
| 2005/0222485 A1 | 10/2005 | Shaw et al. | |
| 2006/0004400 A1 | 1/2006 | McGurk et al. | |
| 2006/0047291 A1 | 3/2006 | Barry | |
| 2006/0100619 A1 | 5/2006 | McClurken et al. | |
| 2006/0130830 A1 | 6/2006 | Barry | |
| 2006/0135955 A1 | 6/2006 | Shadduck | |

(56) References Cited

U.S. PATENT DOCUMENTS

| | | | |
|---|---|---|---|
| 2006/0162731 | A1 | 7/2006 | Wondka et al. |
| 2006/0200076 | A1 | 9/2006 | Gonzalez et al. |
| 2006/0224154 | A1 | 10/2006 | Shadduck et al. |
| 2007/0032785 | A1 | 2/2007 | Diederich et al. |
| 2007/0036417 | A1 | 2/2007 | Argiro et al. |
| 2007/0068530 | A1 | 3/2007 | Pacey |
| 2007/0091087 | A1 | 4/2007 | Zuiderveld |
| 2007/0092864 | A1 | 4/2007 | Reinhardt et al. |
| 2007/0102011 | A1 | 5/2007 | Danek et al. |
| 2007/0106292 | A1 | 5/2007 | Kaplan et al. |
| 2007/0109299 | A1 | 5/2007 | Peterson |
| 2007/0112349 | A1 | 5/2007 | Danek et al. |
| 2007/0118184 | A1 | 5/2007 | Danek et al. |
| 2007/0137646 | A1 | 6/2007 | Weinstein et al. |
| 2007/0293853 | A1* | 12/2007 | Truckai et al. ............... 606/41 |
| 2008/0033493 | A1 | 2/2008 | Deckman et al. |
| 2008/0110457 | A1 | 5/2008 | Barry et al. |
| 2008/0132826 | A1 | 6/2008 | Shadduck et al. |
| 2009/0018538 | A1 | 1/2009 | Webster et al. |
| 2009/0043301 | A1 | 2/2009 | Jarrard et al. |
| 2009/0138001 | A1 | 5/2009 | Barry et al. |
| 2009/0149846 | A1 | 6/2009 | Hoey et al. |
| 2009/0192508 | A1 | 7/2009 | Laufer et al. |
| 2009/0216220 | A1* | 8/2009 | Hoey et al. .................. 606/27 |
| 2009/0312753 | A1* | 12/2009 | Shadduck .................... 606/14 |
| 2010/0094270 | A1 | 4/2010 | Sharma |
| 2010/0204688 | A1* | 8/2010 | Hoey et al. .................. 606/27 |
| 2011/0172654 | A1 | 7/2011 | Barry et al. |
| 2011/0257644 | A1 | 10/2011 | Barry et al. |
| 2011/0270031 | A1 | 11/2011 | Frazier et al. |
| 2013/0006231 | A1 | 1/2013 | Sharma et al. |

FOREIGN PATENT DOCUMENTS

| | | |
|---|---|---|
| EP | 1143864 B1 | 2/2004 |
| EP | 1173103 B1 | 10/2005 |
| EP | 1326549 B1 | 12/2005 |
| EP | 1326548 B1 | 1/2006 |
| EP | 1485033 B1 | 8/2009 |
| WO | WO 00/11927 A2 | 3/2000 |
| WO | WO 01/02042 A1 | 1/2001 |
| WO | WO 02/069821 A1 | 9/2002 |
| WO | WO 03/070302 A1 | 8/2003 |
| WO | WO 03/086498 A2 | 10/2003 |
| WO | WO 2005/025635 A2 | 3/2005 |
| WO | WO 2005/102175 A2 | 11/2005 |
| WO | WO 2006/003665 A2 | 1/2006 |
| WO | WO 2006/052940 A2 | 5/2006 |
| WO | WO 2006/053308 A2 | 5/2006 |
| WO | WO 2006/053309 A2 | 5/2006 |
| WO | WO 2006/055695 A1 | 5/2006 |
| WO | WO 2006/080015 A2 | 8/2006 |
| WO | WO 2006/116198 A2 | 11/2006 |
| WO | WO 2008/051706 A2 | 5/2008 |
| WO | WO 2009/009236 A1 | 1/2009 |
| WO | WO 2009/009398 A1 | 1/2009 |
| WO | WO 2009/015278 A1 | 1/2009 |
| WO | WO 2009/137819 A1 | 11/2009 |
| WO | WO 2010/042461 A1 | 4/2010 |

OTHER PUBLICATIONS

Blacker, G. F.; Vaporization of the uterus; J. of Obstetrics and Gynaecology; vol. 33; pp. 488-511; (year of publication is sufficiently earlier than the effective U.S. filing date and any foreign priority date) 1902.

Carpenter III et al.; Comparison of endoscopic cryosurgery and electrocoagulation of bronchi; Trans. Amer. Acad. Opth.; vol. 84; No. 1; pp. ORL-313-ORL-323; Jan. 1977.

Coda, et al., "Effects of pulmonary reventilation on gas exchange after cryolytic disobstruction of endobronchial tumors," Minerva Medical, vol. 72, pp. 1627-1631, Jun. 1981 (w/ Eng. Trans.).

Eyal et al.; The acute effect of pulmonary burns on lung mechanics and gas exchange in the rabbit; Br. J. Anaesth.; vol. 47; pp. 546-552; (year of publication is sufficiently earlier than the effective U.S. filing date and any foreign priority date) 1975.

Fishman et al., A randomized trial comparing lung-volume-reduction surgery with medical therapy for severe emphysema, N Engl J Med, vol. 348, No. 21, pp. 2059-2073, May 22, 2003.

Goldberg et al.; Radiofrequency tissue ablation in the rabbit lung: Efficacy and complications; Acad. Radiol.; vol. 2; pp. 776-784; Sep. 1995.

Homasson, et al., "Bronchoscopic cryotherapy for airway strictures caused by tumors," Chest, vol. 90, No. 2, pp. 159-164, Aug. 1986.

Kang, Li, "Efficient optimal net surface detection for image segmentation—from theory to practice," M.Sc. Thesis, The University of Iowa, Dec. 2003.

Looga, R. U.; Mechanism of changes in the respiratory and cardiovascular reflexes from the lungs associated with intrapulmonary steam burns; Eng. Trans. from Byulleten Eksperimental not Biologii I Meditsiny; vol. 61; No. 6; pp. 31-33; Jun. 1966.

Marasso, et al., "Cryosurgery in bronchoscopic treatment of tracheobronchial stenosis," CHEST, vol. 103, No. 2, pp. 472-474, Feb. 1993.

Marasso, et al., "Radiofrequency resection of bronchial tumours in combination with cryotherapy: evaluation of a new technique," Thorax, vol. 53, pp. 106-109, (year of publication is sufficiently earlier than the effective U.S. filing date and any foreign priority date) 1998.

Mathur et al., Fiberoptic bronchoscopic cryotherapy in the management of tracheobronchial obstruction, Chest, vol. 110, No. 3, pp. 718-723, Sep. 1996.

Morice et al.; Endobrinchial argon plasma coagulation for treatment of hemotysis and neoplastic airway obstruction, Chest, vol. 119, No. 3, pp. 781-787, Mar. 2001.

Moritz et al.; The effects of inhaled heat on the air pasage and lungs; American Journal of Pathology; vol. XXI; pp. 311-331; (year of publication is sufficiently earlier than the effective U.S. filing date and any foreign priority date) 1944.

Moulding et al.; Preliminary studies for achieving transcervical oviduct occlusion by hot water or low-pressure steam; Advances in Planned Parenthood; vol. 12, No. 2; pp. 79-85; (year of publication is sufficiently earlier than the effective U.S. filing date and any foreign priority date) 1977.

Pracht, Adam; VIDA takes new approach; Iowa City Press-Citizen; Sep. 12, 2005.

Quin, Jacquelyn; Use of neodymium yttrium aluminum garnet laser in long-term palliation of airway obstruction; Connecticut Medicine, vol. 59, No. 7, pp. 407-412, Jul. 1995.

Sutedja, et al., "Bronchoscopic treatment of lung tumors," Elsevier, Lung Cancer, 11, pp. 1-17, Jul. 1994.

Tschirren et al.; Intrathoracic airway trees: segmentation and airway morphology analysis from low-dose CT scans; IEEE Trans. Med. Imaging; vol. 24, No. 12; pp. 1529-1539; Dec. 2005.

Tschirren, Juerg; Segmentation, anatomical labeling, branchpoint matching, and quantitative analysis of human airway trees in volumetric CT images; Ph.D. Thesis, The University of Iowa; Aug. 2003.

Tschirren, Juerg; Segmentation, anatomical labeling, branchpoint matching, and quantitative analysis of human airway trees in volumetric CT images; Slides from Ph.D. defense; The University of Iowa; Jul. 10, 2003.

Van De Velde; Vapo-cauterization of the uterus; Amer. J. Med. Sci.; vol. CXVIII; (year of publication is sufficiently earlier than the effective U.S. filing date and any foreign priority date) 1899.

Vorre et al.; Morphology of tracheal scar after resection with CO2-laser and high-frequency cutting loop; Acta Otolaryngol (Stockh); vol. 107; pp. 307-312; (year of publication is sufficiently earlier than the effective U.S. filing date and any foreign priority date) 1989.

Barry et al.; U.S. Appl. No. 13/860,420 entitled "Methods and Apparatus for Ablating Lung Nodules with Vapor," filed Apr. 10, 2013.

* cited by examiner

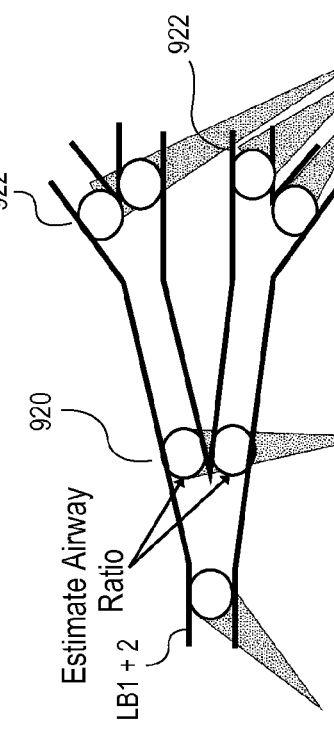

FIG. 10D

| Segment volume: | 508 ml |
| Segment mass: | 43 g |
| Percent of lobe (m÷v): | 54% |
| Tissue to Air Ratio: | 8% |
| Perfusion: | 12% |

FIG. 10E

| Target Vapor Dose: | 10.0 cal/g |
| Vapor Dose Lower Limit: | 7.5 cal/g |
| Vapor Dose Upper Limit: | 10.0 cal/g |
| Flow setting: | 6 |

Suggested treatment location: Sub-Segmental Level

\* A segmental treatment is not suggested because it would be a sub-optimal vapor dose

FIG. 10F

Segment Tx Time (sec)

| 10.0 |
|---|
| 9.4 cal/g |

FIG. 10G

Sub-Segment Tx Time (sec)

| 50% | 50% |
|---|---|
| 5.8 | 5.8 |
| 10.0 cal/g | 10.0 cal/g |
| 33% | 66% |
| 4.2 | 7.4 |
| 10.0 cal/g | 10.0 cal/g |
| 25% | 75% |
| 3.4 | 8.2 |
| 10.0 cal/g | 10.0 cal/g |

Sub-Sub-Segment Tx Time (sec)

| 50% | 50% |
|---|---|
| 3.4 | 3.4 |
| 10.0 cal/g | 10.0 cal/g |

923, 924

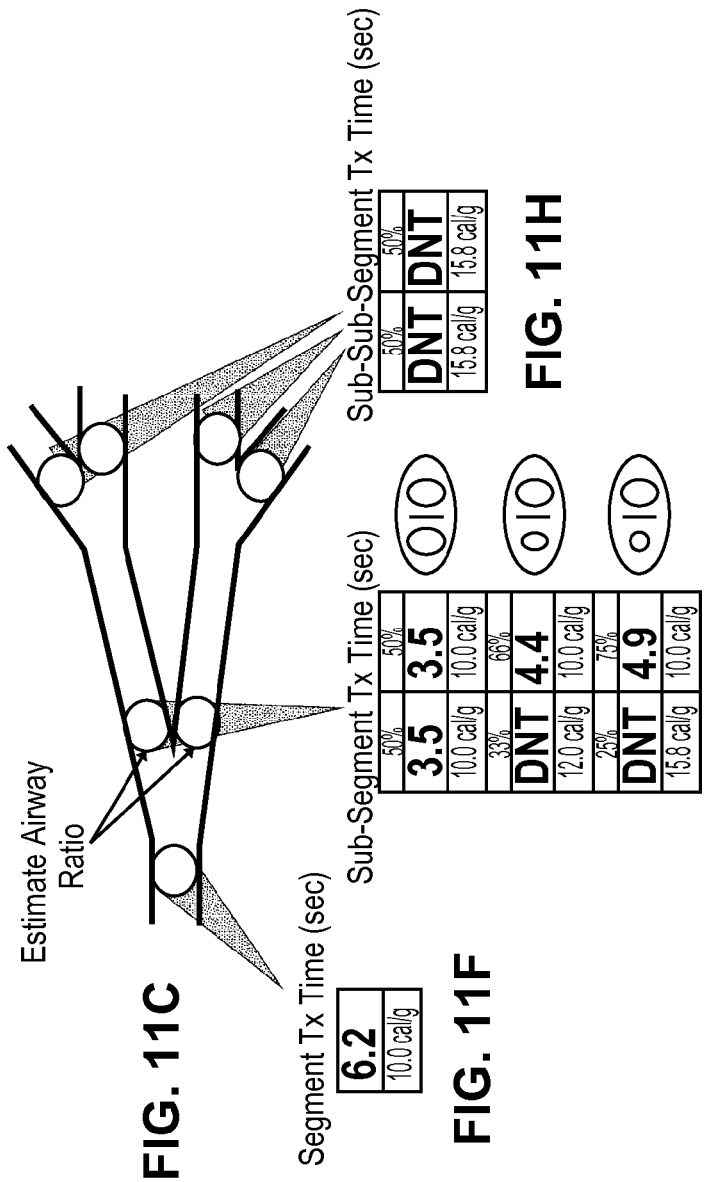

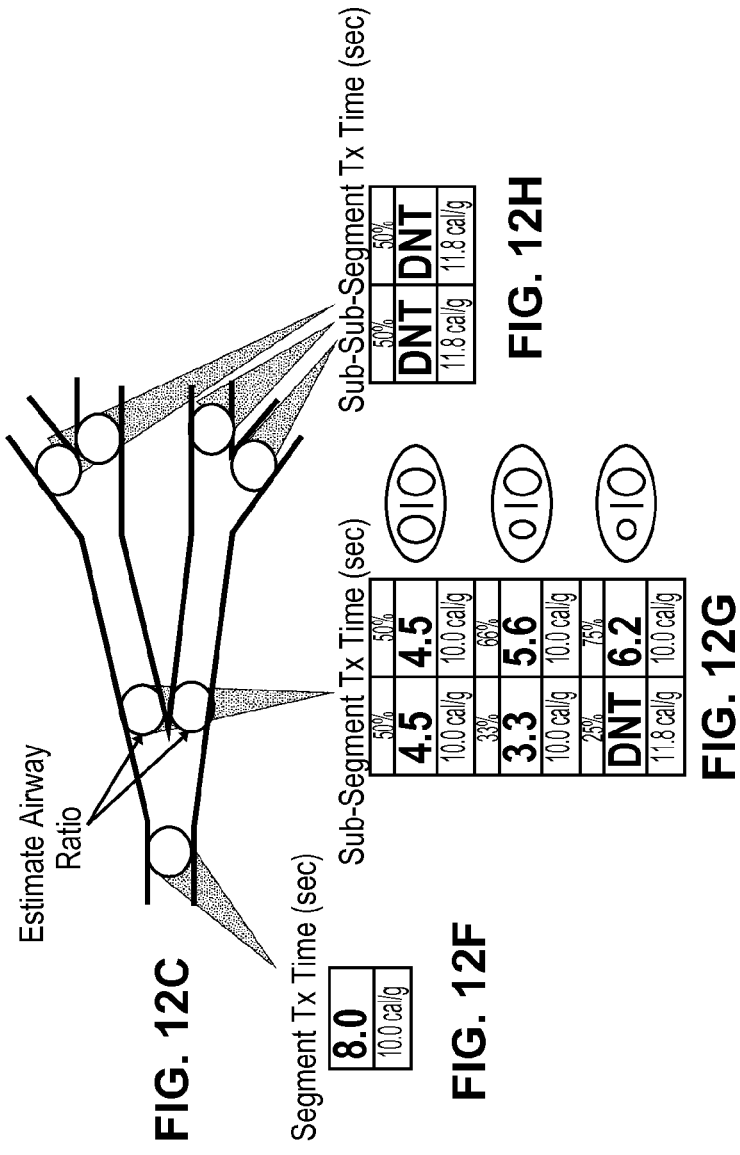

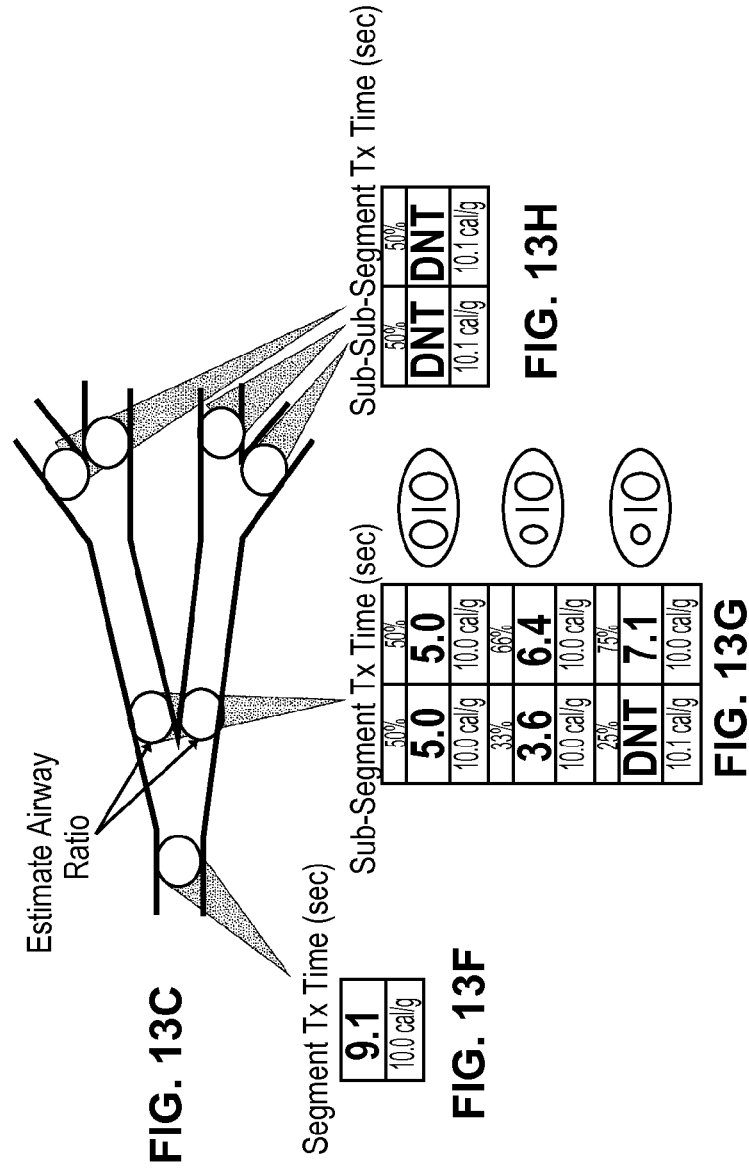

DETERMINING PATIENT-SPECIFIC VAPOR TREATMENT AND DELIVERY PARAMETERS

CROSS REFERENCE TO RELATED APPLICATIONS

This application is a continuation of pending U.S. application Ser. No. 12/409,370, filed Mar. 23, 2009, which claims the benefit under 35 U.S.C. 119 of U.S. Provisional Application No. 61/038,718, filed Mar. 21, 2008, titled "TREATMENT PLANNING METHODS FOR LUNG VOLUME REDUCTION"; and U.S. application Ser. No. 12/409,370 is also a continuation-in-part of U.S. patent application Ser. No. 12/256,197, filed Oct. 22, 2008, now U.S. Pat. No. 8,147,532, which claims priority to U.S. Provisional Application No. 60/981,701, filed Oct. 22, 2007, titled "DETERMINING PATIENT-SPECIFIC VAPOR TREATMENT AND DELIVERY PARAMETERS". These applications are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to medical devices, systems, and methods, and in particular to intrabronchial catheters, systems, and methods for delivering a high pressure, high temperature vapor to one or more tissue targets in a patient's lungs.

BACKGROUND OF THE INVENTION

Chronic Obstructive Pulmonary Disease ("COPD") is a chronic disease of the lungs, in which the fine inner structure of the lungs is destroyed over time, creating large voids within the lung, leading to trapping of inhaled air and loss of lung elasticity (hyperinflation). Common symptoms of COPD (which includes chronic bronchitis and emphysema) are shortness of breath, excessive production of sputum, and chronic cough. Persons suffering from COPD may also experience frequent and sudden worsening of symptoms (exacerbations).

COPD is characterized by pathological changes in the lungs and airways, as prolonged irritation leads to chronic inflammation that often persists even after the source of irritation (e.g., tobacco smoke) is no longer present. COPD is progressive and ultimately life-threatening disorder. Treatment can slow its progression; there is currently no cure.

Most risk factors for COPD are environmental. The most common cause of COPD is exposure to tobacco smoke, including second-hand (passive) smoking. Exposure to indoor and outdoor air pollution, or occupational exposure to dust, particulates, or toxic vapors or fumes can also cause COPD. Frequent lower respiratory tract infections during childhood can also increase susceptibility to COPD.

Current guidelines for the treatment of chronic obstructive pulmonary disease (COPD), including emphysema, call for immediate reduction of patient exposure to risk factors. Risk factors include tobacco smoking and occupational or environmental exposure to particulates or harmful gases. Smoking cessation may be accomplished through patient education and counseling; pharmacotherapeutic intervention may also be effective.

As COPD progresses, medical therapy may be initiated. The standard of care for treatment of stable Stage II (Moderate) and Stage III (Severe) COPD consists of treatment with one or more bronchodilators, including $\beta_2$ agonists, anticholinergic drugs, and methylxanthines administered orally or inhaled via nebulizer. However, there is no evidence that bronchodilators are capable of significantly improving $FEV_1$ or arresting or slowing the inexorable decline in lung function in emphysematous patients. Thus, medical therapy for COPD is primarily used for symptomatic relief, to prevent complications, to increase exercise tolerance, and to treat exacerbations of COPD.

Treatment with inhaled glucocorticosteroids, alone or in combination with bronchodilator therapy, can reduce the frequency of exacerbations and may be indicated in patients with Severe or Very Severe COPD, but is not recommended for patients with mild or moderate COPD as long-term treatment with glucocorticosteroids is associated with steroid myopathy.

Pulmonary rehabilitation, consisting of exercise training programs, nutrition counseling, and patient education are used to treat symptoms of COPD and to improve the patient's overall quality of life, particularly among patients with Stage II (Moderate), Stage III (Severe) and Stage IV (Very Severe) COPD.

Long-term (>15 hours/day) therapy with oxygen ($O_2$) increases survival in patients with COPD and has been shown to improve hemodynamics, exercise tolerance, lung mechanics, and can ameliorate mental deficits incurred through COPD-induced hypoxemia. Patients with COPD receive benefit from long-term oxygen therapy primarily through increased oxygen saturation.

Lung volume reduction surgery (LVRS), in which tissue from one or both lungs is resected in order to treat the physiological consequences of emphysema (enlargement of air spaces, destruction of diffusive capacity, decrease in elastic recoil with consequent reduction in expiratory airflow, hyperinflation, and trapping of air), was first conducted in human subjects in 1957 by Brantigan and Mueller. However, despite patient-reported symptomatic improvement, a high operative mortality rate (18%) precluded its acceptance as a treatment for COPD.

More recently, a series of clinical studies in patients with COPD, including prospective randomized trials, showed that LVRS resulted in benefit for lung function, gas exchange, and quality of life (QOL) measures. The National Emphysema Treatment Trial (NETT) randomly assigned 1218 subjects with severe emphysema to receive pulmonary rehabilitation with or without LVRS. Study results showed statistically significant improvement in exercise capacity among patients receiving both medical therapy and LVRS (15% vs. 3%; P<0.001) and a prespecified subgroup analysis showed a survival advantage at 24 months for patients with predominately upper-lobe emphysema and low baseline exercise capacity who were considered to be at high risk for death from surgery. However, subgroup analysis also suggested that high-risk patients with upper-lobe disease and high initial exercise capacity were poor candidates for LVRS due to increased mortality and lack of significant benefit.

Long-term follow-up of NETT subjects showed a survival benefit for patients assigned to LVRS plus medical therapy overall, as well as lasting improvement in exercise capacity and health-related QOL relative to the medical-therapy-only group. The subgroup of high-risk/high exercise capacity subjects receiving LVRS showed no survival benefit but demonstrated improved exercise capacity.

On the basis of these results, LVRS has been recommended as a palliative treatment for emphysema for the aforementioned sub-groups of patients. LVRS for the treatment of emphysema is also a costly procedure relative to standard medical therapy, and until more data are available, the cost-effectiveness of the procedure remains unclear.

Pharmacological approaches to treating emphysema patients have not yielded significant improvements in large randomized studies. Although LVRS has efficacy benefits, the high mortality and morbidity rates results in high costs. Therefore, minimally invasive approaches (such as bronchoscopic LVR) that decrease mortality and morbidity while offering significant efficacy are desired.

Several bronchoscopic LVR approaches (including plugs, valves and stents) are currently under investigation. Most bronchoscopic approaches involve the blocking or occluding of major airways that supply emphysematous regions of the lung. Bronchoscopic LVR achieved through implantation of one-way endobronchial valves has been explored in human subjects in single-center pilot studies and in larger multi-center studies. In this procedure, one-way endobronchial valves are delivered bronchoscopically to the airway of the emphysematous lung region(s). The goal of the valve is to create collapse or atelectasis of the region of the lung similar to that achieved by LVRS. Initial multicenter experience with endobronchial valves suggests that the therapy is well tolerated, with a 90-day mortality of 1.02%, compared to 7.9% reported for the NETT LVRS study. A total of 53 patients out of 98 (54%) did not demonstrate clinically significant improvement in $FEV_1$ at 90 days, and only 23% showed improvement in exercise tolerance. This lack of improvement is likely attributable to collateral ventilation, which precludes lobar collapse despite occlusion of the major airways.

A bronchoscopic approach that creates consistent LVR despite the presence of collateral ventilation is desired. An approach is also desired that can be tailored, if need be, to safely and effectively treat any patient.

In addition to treating LVR, an approach is also desired that can treat a variety of other lung conditions, such as lung tumors, nodules, infiltrates, bacteria, fungi, viruses and other diseases and conditions.

SUMMARY OF THE INVENTION

The present invention relates generally to using vapor to treat lung tissue. This therapy may be called Bronchoscopic Thermal Vapor Ablation or BTVA.

One aspect of the invention provides a method of applying energy to a patient's lung tissue to reduce the volume of the lung, including the following steps: identifying at least one region of lung including the lung tissue to be treated (such as, e.g., a lung segment or sub-segment); inserting a delivery device into the lung region; and delivering vapor through the delivery device to the lung tissue to be treated at a dose between about 5 calories/gram to about 40 calories/gram, wherein the vapor undergoes a phase change to liquid, and energy released during the phase change is transferred to the lung tissue to injure the tissue. Some embodiments includes the step of heating the vapor to at least 100° C. before delivering the vapor in, e.g., a vapor generator disposed outside the patient.

The effects of the delivered vapor dose may vary. In some embodiments, the dose delivered causes the lung volume to be reduced over a period of about 4 to about 8 weeks. In some embodiments, the dose delivered causes the lung volume to be immediately reduced from shrinking and or denaturing of collagen. The energy transferred to the tissue may also cause coagulative necrosis of the lung tissue, possibly followed by fibrosis to effectively reduce the volume of the lung region. In some embodiments, the energy transferred to the tissue causes substantially no thermal fixation. In some embodiments, the delivering step includes the step of ablating microvasculature in the lung tissue.

In some embodiments, the step of delivering the vapor includes the step of delivering the vapor at a flow rate of between about 20 calories/second to about 200 calories/second. The vapor may be delivered for a duration of between about 2 seconds to about 30 seconds, or possibly for a duration between about 4 and about 10 seconds, in some embodiments. The delivered dose may be, e.g., between about 5 cal/g and about 20 cal/g, between about 5 cal/g and about 10 cal/g., or between about 20 cal/g and about 40 cal/g.

Another aspect of the invention provides a method of determining treatment parameters for applying energy to lung tissue with vapor to selectively injure the tissue, the method including the following steps: imaging at least one region of the lung including the lung tissue to be treated; determining a parameter (such as, e.g., mass and/or volume) of the lung tissue of the region to be treated based on the imaging; determining a safe and efficacious dosage for treating the tissue to cause a specific degree of injury to the lung tissue; determining an amount of energy to be delivered to the region based on the parameter of the lung tissue and the dose; and determining a duration for delivering the vapor based on the amount of energy to be delivered and an energy flow rate of a vapor delivery system. In some embodiments, the specific degree of injury to the lung tissue comprises coagulative necrosis which, in some embodiments, may cause fibrosis of the lung tissue to effectively reduces the volume of the lung.

Some embodiments of the invention also include the step of delivering the vapor to the segment of the lung at the delivery rate and for the determined duration. The vapor may be heated to at least 100° C. before delivering the vapor. In some embodiments, delivering the vapor causes the vapor to change to liquid, and the energy released during the phase change is transferred to the lung tissue of the segment or sub-segment.

In some embodiments, the step of imaging the at least one region of the lung to be treated includes the step of taking a CT scan of the at least one segment or sub-segment of the lung. The at least one segment or sub-segment of the lung to be treated may be at least one of RB1, RB2, RB3, LB1, LB2, and LB3.

In some embodiments, the step of determining an amount of energy to be delivered includes the step of multiplying the mass of the segment or sub-segment and the dosage. In some embodiments, the duration for delivering the vapor is determined by dividing the amount of energy to be delivered by the energy delivery rate of the delivery system. In some embodiments, for example, the safe and efficacious dosage for treating the tissue is between about 5 cal/g and about 40 cal/g., and the energy flow rate of the delivery system is between about 20 calories/second and about 200 calories/second.

Yet another aspect of the invention provides a method of determining treatment parameters for applying energy to lung tissue with vapor to reduce the volume of the lung, including the following steps: imaging at least one segment to be treated of the lung tissue; determining a mass of the segment to be treated based on the imaging; determining a safe and efficacious dosage for treating the segment to be treated to cause a specific degree of injury to the lung tissue; determining an amount of energy to be delivered to the segment to be treated based on the mass of the segment to be treated and the dose; and determining a duration for delivering the vapor based on the amount of energy to be delivered and an energy flow rate of a vapor delivery system.

In one embodiment, the method further comprises calculating at least one tissue-to-air ratio by dividing the mass of the at least one segment to be treated by the mass of the air within the at least one segment to be treated. In some embodiments, the vapor is delivered to the segment to be treated at the delivery rate and for the determined duration if the tissue-to-air ratio is above a predetermined level. In one embodiment, the predetermined level is 4%.

In other embodiments, the vapor is delivered to a superior lobe of a lung if the tissue-to-air ratio of the superior lobe of the lung is less than the tissue-to-air ratio of an inferior lobe of the lung. In another embodiment, the vapor is delivered to an inferior lobe of a lung if the tissue-to-air ratio of the inferior lobe of the lung is less than the tissue-to-air ratio of a superior lobe of the lung.

In yet another embodiment, the vapor is delivered to a first lung if the tissue-to-air ratio of the first lung is less than the tissue-to-air ratio of a second lung. In one embodiment, the vapor is delivered to a superior lobe of the first lung. In another embodiment, the vapor is delivered to an inferior lobe of the first lung.

Some embodiments determine the perfusion of the lung tissue to be treated. In some embodiments, the vapor is delivered to a superior lobe of a lung if a perfusion of the superior lobe of the lung is less than a perfusion of an inferior lobe of the lung. In another embodiment the vapor is delivered to an inferior lobe of a lung if a perfusion of the inferior lobe of the lung is less than a perfusion of a superior lobe of the lung.

In other embodiments, the perfusion heterogeneity of the lungs is determined. In on embodiment, the vapor is delivered to a first lung if a perfusion heterogeneity of the first lung is greater than a perfusion heterogeneity of a second lung.

One embodiment includes system for determining treatment parameters and applying energy to lung tissue with vapor to selectively injure the tissue, the system comprising: an imaging system adapted to image at least one segment of the lung tissue to be treated; a vapor generator adapted to generate a heated water vapor; a delivery catheter coupled to the vapor generator; and an electronic controller integral to the system, the electronic controller configured to determine a mass of the segment to be treated based on the imaging, determine a safe and efficacious dosage for treating the segment to be treated to cause a specific degree of injury to the lung tissue, determine an amount of energy to be delivered to the segment to be treated based on the mass of the segment to be treated and the dose, and determine a duration for delivering the vapor based on the amount of energy to be delivered and an energy flow rate of a vapor delivery system.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A-9H are illustrations of treatment plans or treatment guides for aiding a physician in delivering vapor to lung tissue, according to one embodiment.

FIGS. 10A-10H are illustrations of treatment plans or treatment guides for aiding a physician in delivering vapor to lung tissue, according to another embodiment.

FIGS. 11A-11H are illustrations of treatment plans or treatment guides for aiding a physician in delivering vapor to lung tissue, according to yet another embodiment.

FIGS. 12A-12H are illustrations of treatment plans or treatment guides for aiding a physician in delivering vapor to lung tissue, according to one particular embodiment.

FIGS. 13A-13H are illustrations of treatment plans or treatment guides for aiding a physician in delivering vapor to lung tissue, according to one embodiment.

DETAILED DESCRIPTION OF THE INVENTION

Figure 1:
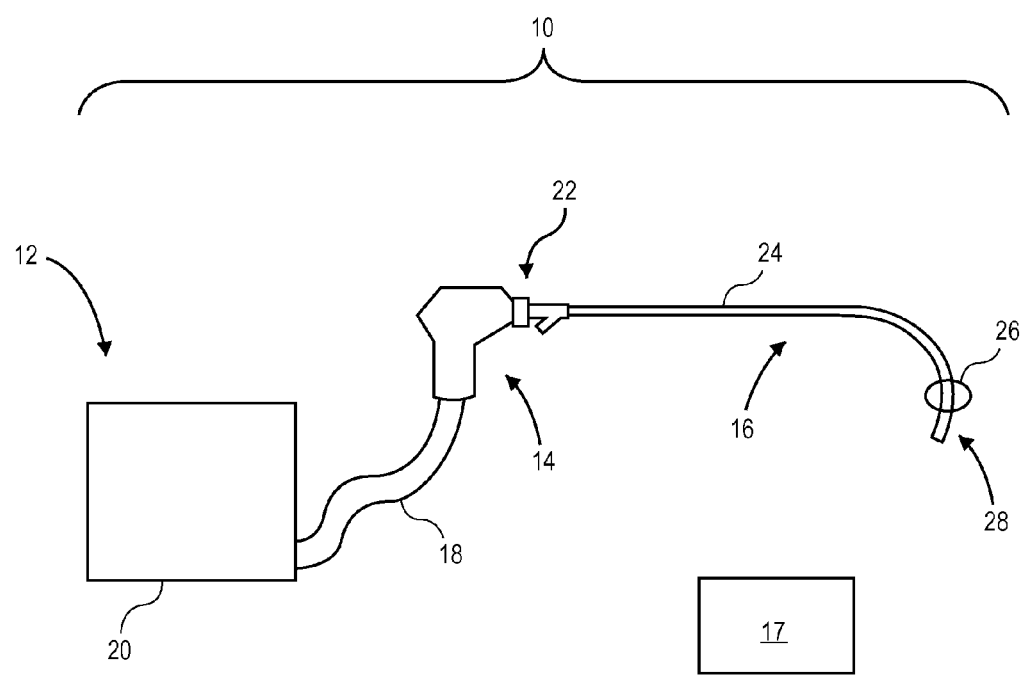
FIG. 1 shows a system for generating and delivering therapeutic vapor to a lung.

The present invention relates generally to using vapor to treat lung tissue. This therapy may be called Bronchoscopic Thermal Vapor Ablation or BTVA. In general, the transfer of energy to an emphysematous lung region may result in ablation of micro vascularization which would reduce the amount of blood flowing to that region. This reduction in blood flow, along with the reduction in ventilation to poorly functioning regions of lung, can result in more blood flow to better functioning regions of lung. This can result in an increase in diffusion capacity (DLCO). Increases in DLCO can result in several potential benefits to the patient including increase in exercise capacity, reduction in dyspnea (shortness of breath) and reduction in the need for supplemental oxygen.

The application of vapor can invoke lung growth which may result in an increase in pulmonary flow and or parenchyma volume or mass that might result in increased diffusion capacity (DLCO) without measurable changes in Residual Volume (RV), FEV1, FRC or other mechanical pulmonary function measures. Increases in DLCO can result in several potential benefits to the patient including increase in exercise capacity, reduction in dyspnea, and reduction in the need for supplemental oxygen. The reduction in blood flow and ventilation by virtue of LVR may also result in an increase in the matching of perfusion and ventilation (VQ match).

More specifically, the invention relates to determining delivery parameters (e.g., vapor dose, flow rate of a delivery system) for delivering vapor to the lung to induce a desired degree of injury to the tissue. The energy transferred to the tissue causes injury and subsequent lung growth signals that stimulate new lung tissue in either the treated region of lung or throughout the entire lung. Treatment of the lung as used herein refers to substantially immediate effects on the lung tissue as well as effects over a longer period time, and can be on the order of weeks, months, or even years. The delivery parameters can depend on the amount (e.g., mass or volume) of lung to be treated as well as the desired degree of injury to the tissue (e.g., coagulative necrosis, thermal fixation).

While delivering vapor to the lung to cause tissue fibrosis to reduce the volume of the lung is one use of vapor treatment, it is understood that the invention includes administering vapor to the lung to treat a variety of conditions and diseases. For example, vapor can be used in the treatment of tumors, lung cancer, solitary pulmonary nodule, lung abscesses, tuberculosis, and other lung diseases. The condition to be treated, and specifically the desired degree of injury (immediate and/or longer term) to the lung tissue, can partially determine the treatment and delivery parameters.

One type of injury that may be a desired result of the vapor treatment is coagulative necrosis or fibrosis. Coagulative necrosis regions are generally characterized by tissue in which sufficient thermal tissue injury occurred to result in cell death without causing thermal fixation. Subsequently, the tissue undergoes the reabsorption and the classical pathway of wound healing with subsequent fibrosis (scar) formation. The LVR described herein is generally accomplished by fibrosis of the lung tissue following vapor treatment.

Thermal fixation is generally characterized by dead tissue that received sufficient hyperthermic exposure to morphologically mimic chemical (formalin) fixation. The exposure is sufficient to completely denature cellular and extracellular matrix proteins in situ so that the natural processes of enzymatic tissue autolysis and breakdown after lethal injury are inhibited. As a result, the tissue resists reabsorption and remodeling via a wound healing pathway and is generally walled off by the body similar to a foreign body.

Other types or degrees of injury that may be desired to induce in lung tissue include pulmonary edema, hyaline membranes, acute or chronic inflammation, post-obstructive change, atelectasis, and bronchial, bronchiole, and alveolar parenchyma with minimal to absent histologic injury.

When vapor is delivered to the target lung tissue, it undergoes a phase change from vapor to liquid. The thermal energy released during this phase change is transferred to the lung tissue. This rapidly heats the tissue and induces such injuries as coagulative necrosis (followed by fibrosis), thermal fixation, tissue collapse, shrinkage, neointima hyperplasia, or any other desired injury to the lung tissue such as those described above. Thermal energy may also be conducted to the tissue from the hot vapor and/or vapor condensate.

Fibrosis following necrosis can produce a reduction in volume of the lung (due to the volumetric reduction of non-viable lung tissue). By reducing lung size, the remaining lung and surrounding muscles (intercostals and diaphragm) are able to work more efficiently. This can make breathing easier and help patients achieve improved quality of life allow for improved breathing mechanics, including increased volume per breath and $O_2$ uptake increase.

The volume of the lung may also be immediately reduced (as opposed to fibrosis which generally causes reduction in volume over a longer period of time) from shrinking and or denaturing of collagen.

The degree of LVR is generally dose dependent; the higher the dose, the more the lung volume is reduced. The degree of LVR may not be determined until weeks or months after treatment. In some embodiments the dose dependency of the LVR may not begin to be apparent until about 2 to about 4 months. This gradual reduction in LVR may help prevent or minimize acute tearing of pre-existing adhesions that can produce pneumothorax in some emphysema patients.

Another advantage to using vapor treatments described herein to reduce the volume to the lung is that this technique can be an effective method even in the presence of collateral ventilation.

In addition to the desired degree of injury (which depends on the lung condition to be treated), the amount of lung tissue to be treated will partially determine the treatment parameters. For example, the delivery parameters could be different for treating an entire lobe of the lung as opposed to treating a segment or sub-segment of a lobe. As used herein, lung tissue includes both native lung tissue in addition to any other growth or non-lung tissue that may be present in or on the lung, such as, for example without limitation, a tumor.

FIGS. 1-5 show an exemplary system and system components for generating and delivering vapor to lung tissue to be treated. The system 10 generally comprises a vapor generator 12, hand-piece 14, and delivery catheter 16. The system may further include a medical imaging system 17, such as a CT, MRI, ultrasound, or x-ray imaging system.

The vapor generator 12 is attached to the hand-piece 14 by tube 18. The generator comprises a pressure vessel 20 containing liquid water (or other biocompatible liquid, such as saline or ethanol) and steam (not shown), a heating element (not shown) to heat the water, sensors (not shown), and valves (not shown). Hand piece 14 is coupled to the proximal end 22 of catheter.

The catheter is generally used to deliver the heated water vapor (steam) via a bronchoscope (not shown) to a targeted segment or sub-segment of the subject's lung. The catheter 16 generally is comprised of flexible shaft 24 and occlusion balloon 26 located at or slightly proximal to the distal end 28 of the catheter.

Figure 4:
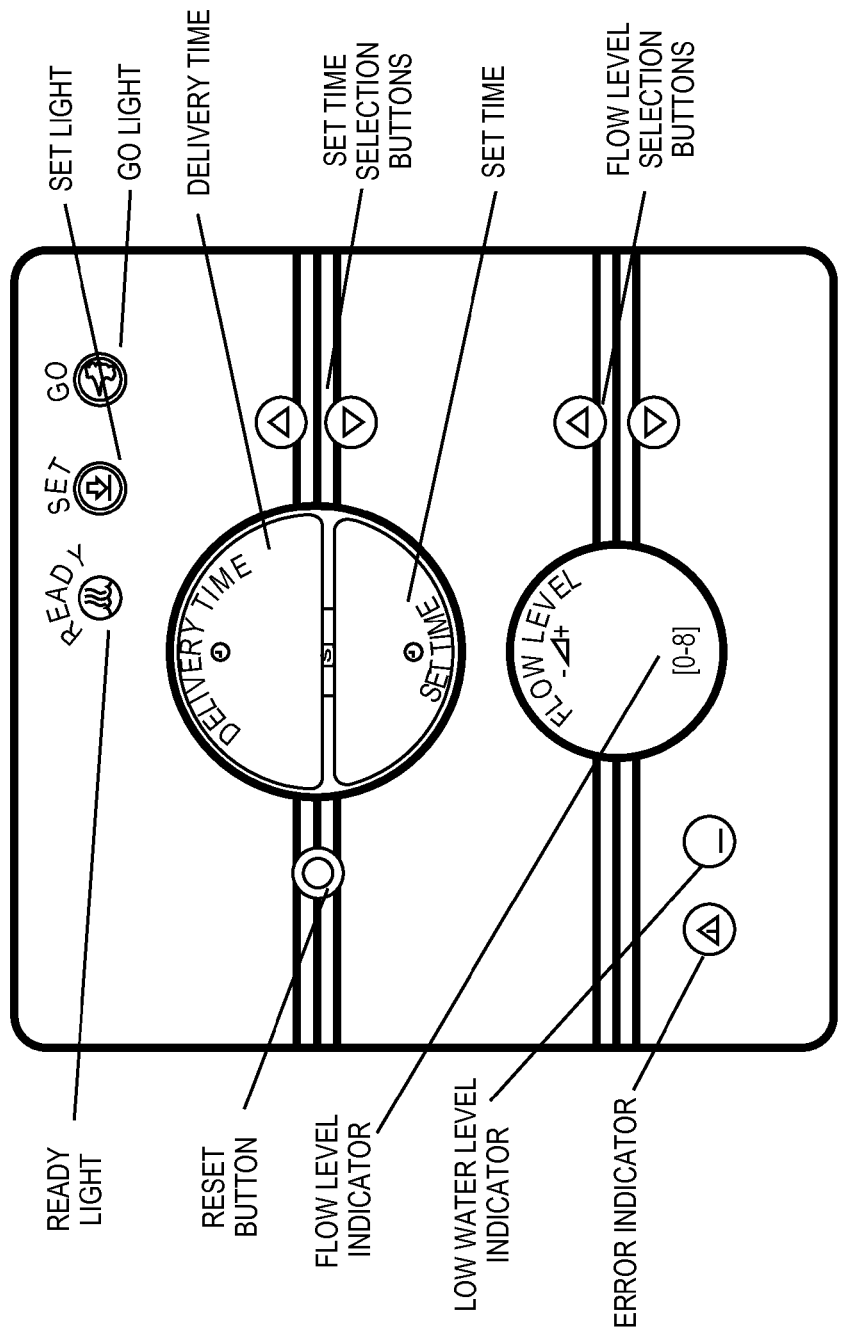
FIG. 4 shows a user interface for use with the system of FIG. 1.

The vapor generator is an electronically controlled pressure vessel that can generate and deliver precise amounts of steam or vapor via the catheter. In some embodiments, the vapor is generally heated to between about 100° C. to about 175° C. The operator can select the flow level and the duration of the vapor treatment (the determination of which is described below) using a user interface on the front panel. An exemplary user interface is shown in FIG. 4 and can include, among other components, controls to adjust the delivery time and/or flow level of vapor. In another embodiment, the flow level and duration of the vapor treatment may be automatically selected by an electronic controller (not shown) integral to the system 10 or generator 12 based on measured patient parameters, described below. The combination of flow level and delivery time delivers a specific amount of vapor therapy to the patient. While delivery of vapor to the patient is preferably manually triggered by the operator using the hand-piece, an electronic controller inside the generator can continuously monitor temperatures, pressures, water level, to ensure safety of the software.

Figure 2:
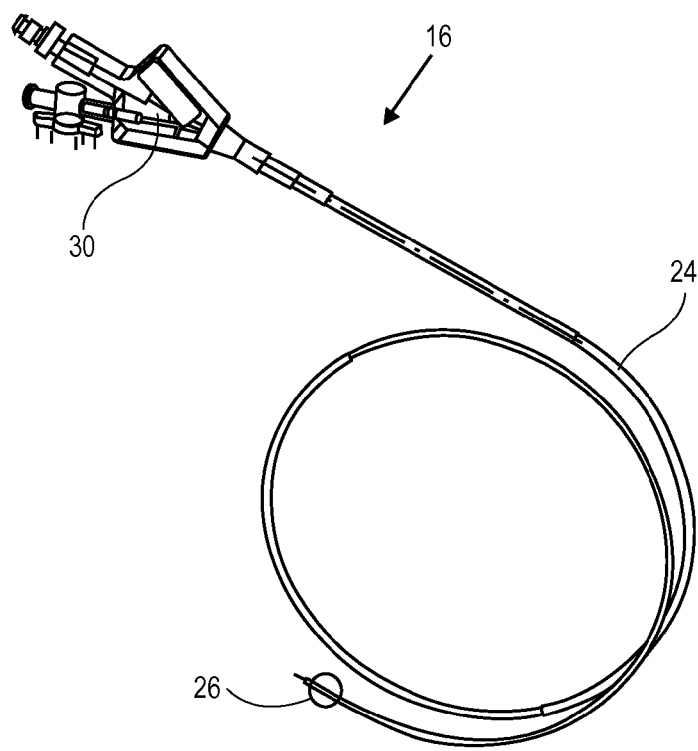
FIG. 2 shows details of a vapor delivery catheter component of the system of FIG. 1.
Figure 3:
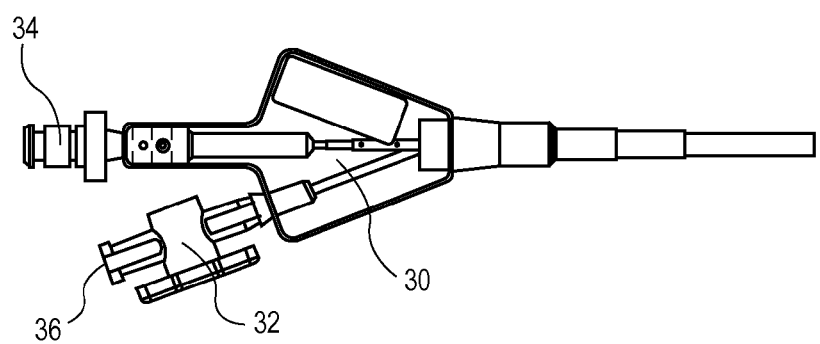
FIG. 3 shows details of the vapor delivery catheter of FIG. 2.

The catheter is preferably non-reusable and supplied sterile. It can be comprised of components for occluding the target airway and delivering a dose of vapor from the vapor generator to the targeted lung segment or sub-segment. As shown in FIGS. 2-3, manifold 30 can be located at the proximal end of the catheter and contain stopcock 32 for attachment of a standard syringe (not shown) to luer connector 36 to inflate a compliant balloon, as well as quick-connect 34 for coupling the catheter to the hand-piece. The catheter shaft can be adapted to allow delivery of the catheter through a bronchoscope, and the catheter can comprise a balloon near the distal end of the catheter shaft to allow proper sealing of the targeted bronchi.

Figure 5:
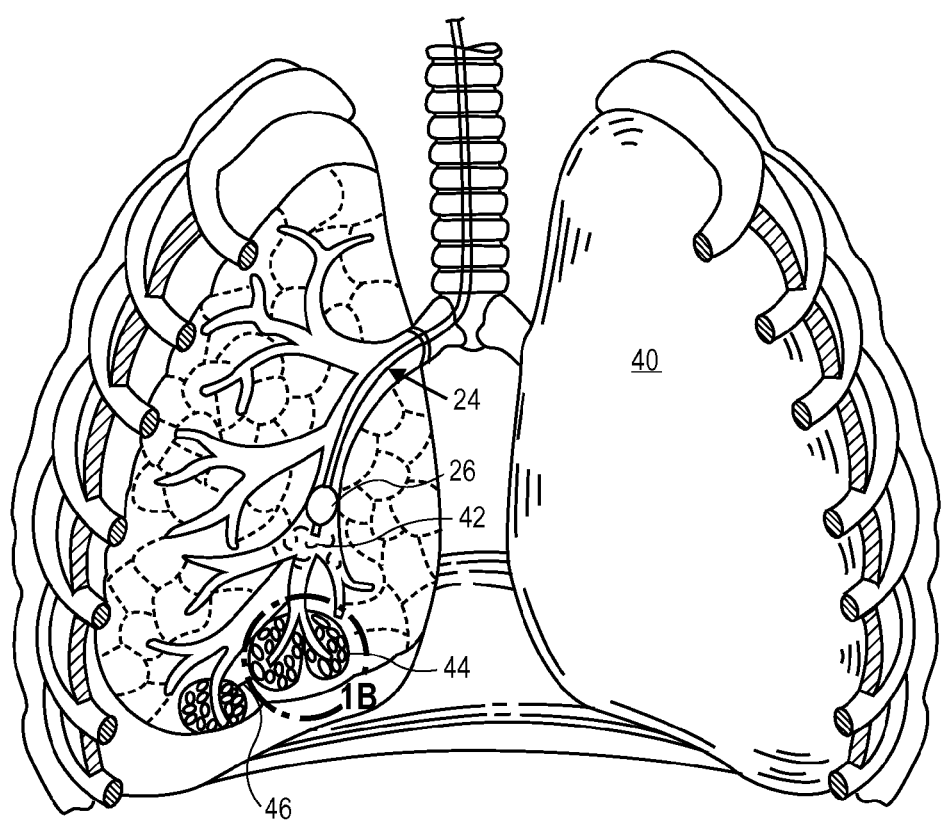
FIG. 5 shows the system of FIG. 1 in use to treat a patient's lung.

FIG. 5 illustrates an exemplary method of treating a patient's lung 40. The method can comprise the steps of advancing flexible shaft 24 into the region of the lung targeted for treatment, such as a segment or sub-segment of the lung. The occlusion balloon 26 at or near the distal end of the flexible shaft can be inflated to seal the airway in the lung. The vapor 42 can then delivered from the distal end of the flexible shaft into the region of the lung target for treatment. Delivering the vapor to the target tissue is intended to injure the tissue of the air sac or alveoli 44, the tissue of terminal bronchioles and tissue of collateral passageways 46. The balloon can then deflated and the catheter can be withdrawn.

Methods of determining treatment parameters and applying vapor energy to lung tissue to bring about a desired injury to the target tissue (e.g., necrosis/fibrosis, thermal fixation) will now be described.

Figure 6:
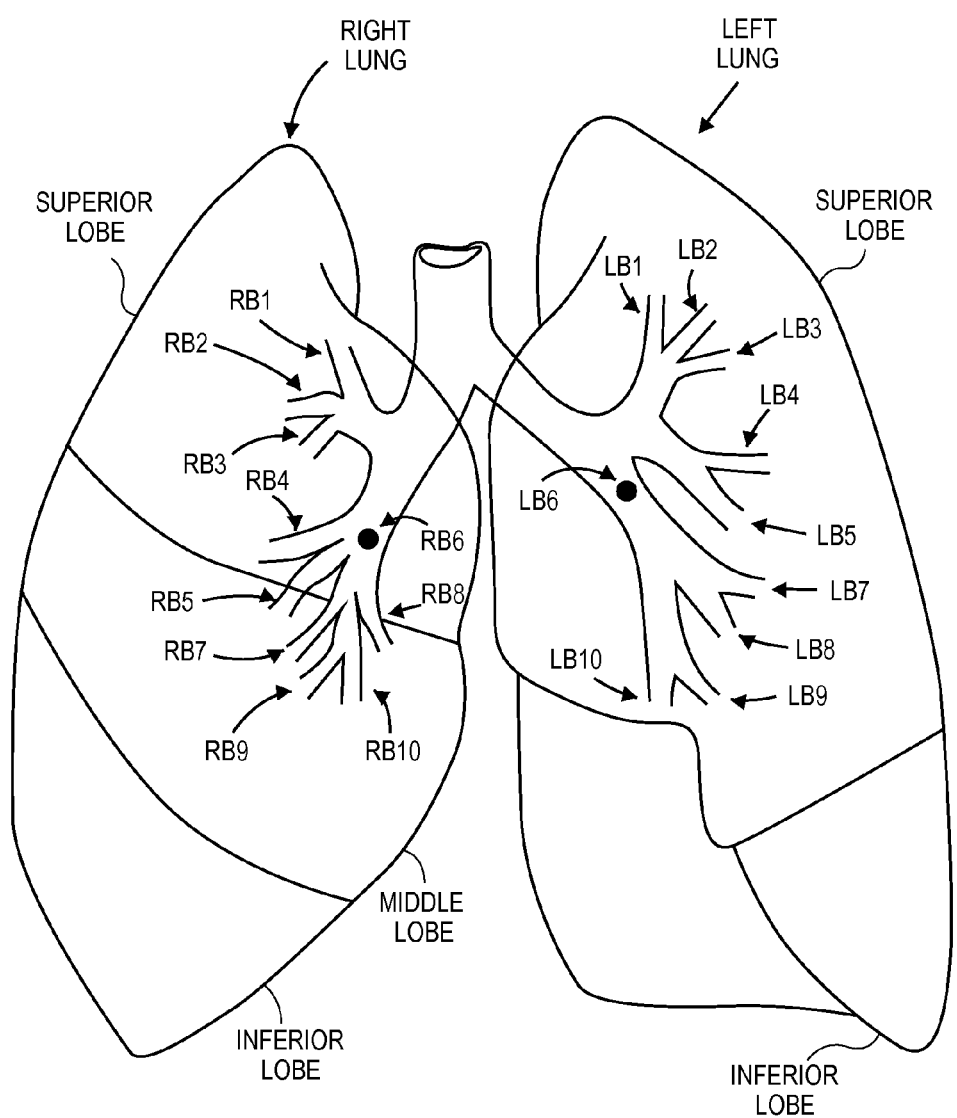
FIG. 6 is a schematic drawing of a patient's lungs.

Understanding the anatomy of the lung will aid in description of the methods of treatment below. FIG. 6 is a schematic drawing showing an anterior view of the left and right lungs of a patient. The left lung is divided into two lobes; the superior lobe and the inferior lobe, and the right lung is divided into three lobes; the superior lobe, the middle lobe, and the inferior lobe. As shown in FIG. 6, the left lung includes 8 segmental bronchi, also referred to as tertiary bronchi, and the right lung includes 10 segmental bronchi.

The segmental bronchi of the superior lobe of the left lung comprise the apical (LB1), posterior (LB2), anterior (LB3), superior lingular (LB4), and inferior lingular (LB5) segments. The LB1 and LB2 segments can also be referred to as the apicoposterior segment (LB1+2). The segmental bronchi of the inferior lobe of the left lung comprise the superior (LB6), anterior basal (LB7), medial basal (LB8), lateral basal (LB9), and posterior basal (LB10). The LB7 and LB8 segments can be referred to as the anteromedial basal segment (LB7+8).

The segmental bronchi of the superior lobe of the right lung comprise the apical (RB1), posterior (RB2), and anterior (RB3) segments. The segmental bronchi of the middle lobe of the right lung comprise the lateral (RB4) and medial (RB5) segments. The segmental bronchi of the inferior lobe of the right lung comprise the superior (RB6), anterior basal (RB7), medial basal (RB8), lateral basal (RB9), and posterior basal (RB10) segments.

Figure 7:
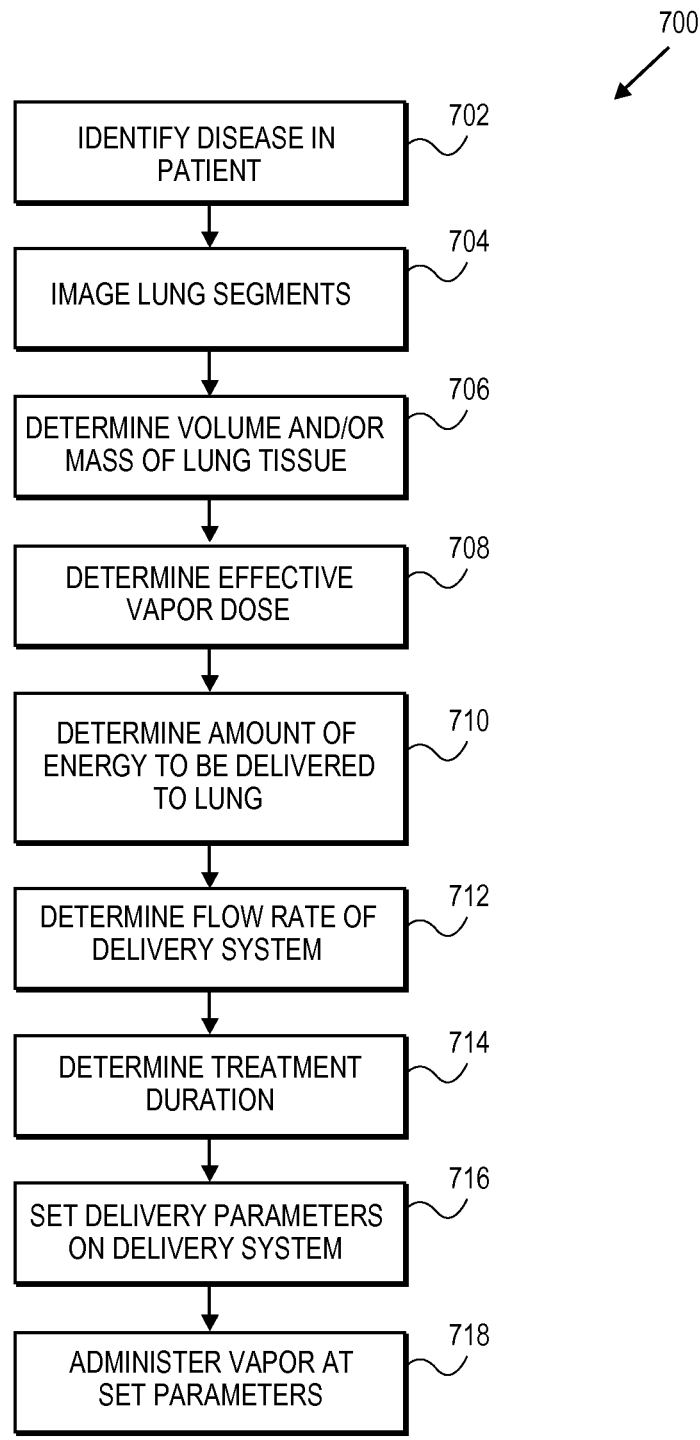
FIGS. 7-8 are flow charts illustrating exemplary methods for determining vapor delivery parameters to treat lung tissue.

FIG. 7 is a flowchart 700 describing a method of determining treatment parameters to treat the lungs of a patient based on the volume and/or mass of lung tissue. At step 702, the method can include identifying a lung condition or disease to be treated (e.g., COPD, a lung tumor). Identifying a lung condition or disease, such as COPD or a lung tumor, can be accomplished by known medical tests and procedures.

At step 704, the method can further include imaging at least one lobe, segment, or sub-segment of the lung to be treated. Imaging a segment or sub-segment of the lung to be treated can be performed by a number of medical imaging techniques or medical imaging systems, such as, without limitation, CT, MRI, ultrasound, and x-ray.

At step 706, the method can include determining an amount (e.g., the mass or volume) of the lung tissue of the lobe, segment, or sub-segment to be treated based on the imaging. The volume and/or density determinations of the amounts of tissue in each lung to be treated can be performed using such software as VIDA Emphysema Profiler 1.1 software (VIDA Diagnostics, Inc. Iowa City, Iowa USA). Further information on lung airway segmentation using CT can be found in Intrathoracic airway trees: segmentation and airway morphology analysis from low-dose CT scans. Tschirren, J.; Hoffman, E. A.; McLennan, G.; Sonka, M., Medical Imaging, IEEE Transactions on, Volume 24, Issue 12, December 2005 Page(s): 1529-1539. In addition to modeling of the patient's airways, VIDA software (as well as the algorithms described in patent application Ser. No. 11/542,016, filed Oct. 2, 2006) can also generate parameters of different segments in a patient's lungs. However, other software, algorithms, or methods can be used to determine the total volume of each lung, lobe and/or segment. In one embodiment, the electronic controller in generator 12 of FIG. 1 can determine the amount of lung tissue of the lobe, segment, or sub-segment to be treated. In another embodiment, the amount of lung tissue can be determined external to the generator, such as by a physician or clinician.

At step 708, the method can further include determining an effective vapor dose to be delivered to the lobe, segment or sub-segment based. A safe and efficacious dose of energy (e.g., calories/gram) to be applied to the lung tissue must be determined depending on the desired degree of injury for the lung tissue. In general, as the dose increases the degree of injury to the tissue increases. Doses of vapor from about 5 cal/g to about 40 cal/g will generally result in coagulative necrosis with little, or even no, thermal fixation. In one embodiment, a target vapor dose is approximately 10 cal/g. The degree of thermal fixation will generally increase as the dose increases above 40 cal/g. The desired degree of injury to the lung tissue can therefore be controlled by altering the dose of vapor applied to the tissue. In one embodiment, the electronic controller in generator 12 of FIG. 1 can determine the effective vapor dose to be delivered to the lobe, segment, or sub-segment to be treated. In another embodiment, the effective vapor dose can be determined external to the generator, such as by a physician or clinician.

To cause necrosis, the energy dose in some embodiments varies from about 5 cal/g to about 40 cal/g. These limits are, however, not intended to be definitive limitations of the doses applied, as other delivery parameters described below (e.g., delivery rate, delivery duration, etc.) may allow different doses to be applied to accomplish the same or similar injury to the tissue.

At step 710, the amount of total energy that needs to be applied by the delivery system to the tissue can be determined. This is generally accomplished by multiplying the dose from step 708 by the amount of tissue to be treated from step 706 to determine the total amount of energy to deliver. For example, the dose, in calories per gram, multiplied by the amount of tissue, in grams, will result in the total amount of calories to be delivered to the target tissue. In one embodiment, the electronic controller in generator 12 of FIG. 1 can determine the amount of total energy that needs to be applied by the delivery system to the lobe, segment, or sub-segment to be treated. In another embodiment, the amount of total energy that needs to be applied by the delivery system can be determined external to the generator, such as by a physician or clinician.

At step 712, the flow rate of the delivery system can be determined. The flow rate is generally between about 20 cals/second to about 200 cals/second. Again, these limitations are not intended to be definitive limitations and the delivery rate may be higher or lower depending on other treatment and/or delivery parameters. In one embodiment, the electronic controller in generator 12 of FIG. 1 can determine the flow rate of the delivery system. In another embodiment, the flow rate of the delivery system can be determined external to the generator, such as by a physician or clinician.

At step 714, the method can further include determining the treatment duration for delivering the vapor to the lungs. The treatment duration can be calculated by dividing the total amount of energy to be delivered from step 710 (calories) by the energy flow rate from step 712 (calories per second). For example, to deliver 300 calories to a segment of the lung at a flow rate of 30 cals/second, the treatment duration would be 10 seconds. In one embodiment, the electronic controller in generator 12 of FIG. 1 can determine the treatment duration for delivering the vapor to the lungs. In another embodiment, the treatment duration for delivering the vapor to the lungs can be determined external to the generator, such as by a physician or clinician.

At step 716, the delivery parameters can be set on the delivery system, such as flow rate from step 712 and treatment duration from step 714. These parameters can typically be set via controls on a delivery system, such as on the user interface in FIG. 4. Once the user sets the flow rate, the generator can establish the requisite amount of pressure in the generator to deliver the vapor at the desired flow rate by adjusting the amount of heat applied in the generator. Changing the flow rate setting can cause the generator to adjust the amount of pressure in the generator. The pressure in the vapor generator can range from between about 10 psi (69 kPa) to over about 100 psi (689 kPa), for example. In another embodiment, the delivery parameters do not need to be manually set by a user, but instead can be automatically set by an electronic controller in the generator, for example.

Treatment times can vary depending on the volume, mass to be treated, and the desired injury to the tissue. Treatment times can vary from about 2 seconds to about 30 seconds. In some embodiments for causing necrosis to reduce the volume of the lung, the safe and effective treatment time is between about 4 and about 10 seconds. To thermally fix the lung, for example, the treatment time may be longer in order to injure the tissue to a greater degree.

At step 718, the vapor can be administered to the lungs of the patient at the set parameters.

Figure 8:
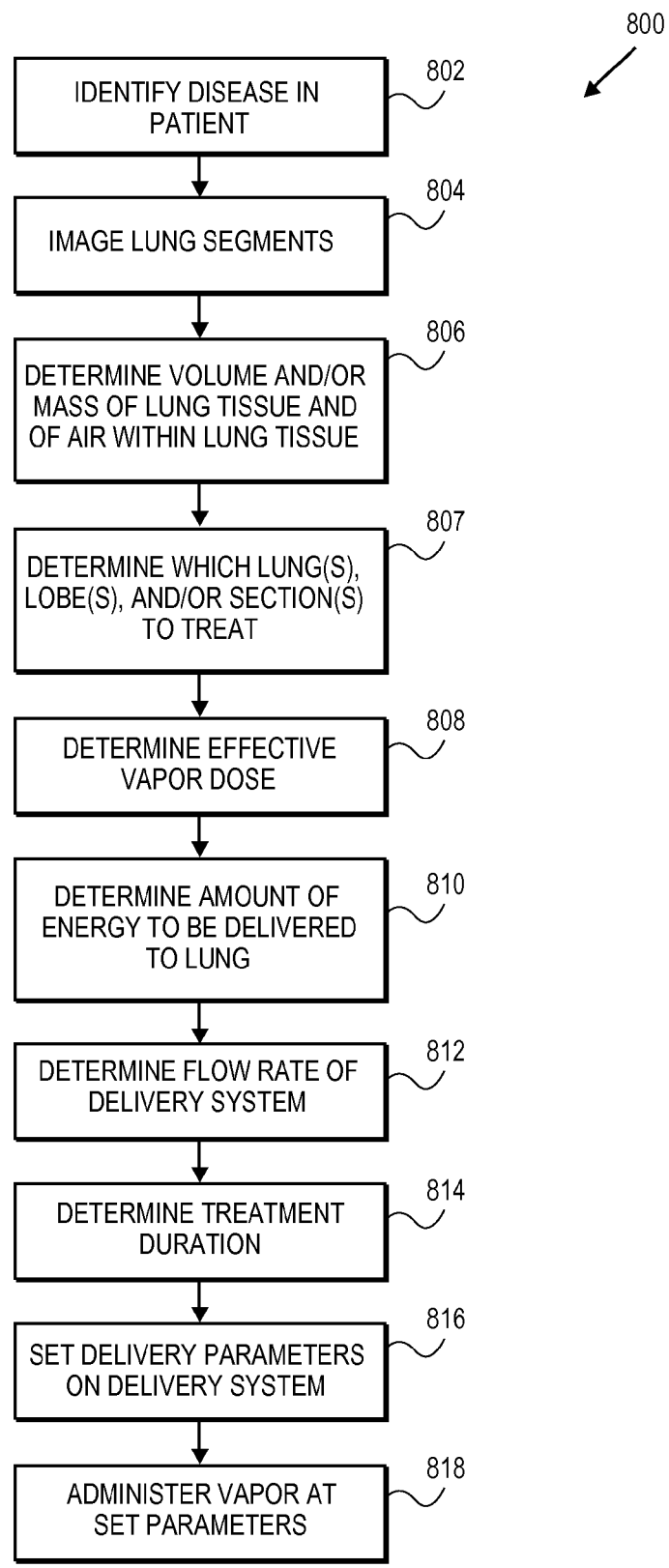

FIG. 8 is a flowchart 800 describing a method of determining treatment parameters to treat the lungs of a patient based on the volume and/or mass of lung tissue as well as the volume and/or mass of air within the lung tissue. Many of the steps of flowchart 800 are the same as steps described above in flowchart 700 of FIG. 7. At step 802, the method can include identifying a lung condition or disease to be treated (e.g., COPD, a lung tumor). Identifying a lung condition or disease, such as COPD or a lung tumor, can be accomplished by known medical tests and procedures.

At step 804, the method can further include imaging at least one lobe, segment, or sub-segment of the lung to be treated. Imaging a segment or sub-segment of the lung to be treated can be performed by a number of medical imaging techniques, such as, without limitation, CT, MRI, ultrasound, and x-ray.

At step 806, the method can include determining an amount (e.g., the mass or volume) of the lung tissue of the lobe, segment, or sub-segment to be treated based on the imaging. This step also includes determining an amount (e.g., the mass or volume) of the air within the lung tissue of the lobe, segment, or sub-segment to be treated based on the imaging. The volume and/or density determinations of the amounts of tissue and air in each lung to be treated can be performed using such software the VIDA Emphysema Profiler software, as described above. However, other software, algorithms, or methods can be used to determine the total volume of each lung, lobe and/or segment. In one embodiment, the electronic controller in generator 12 of FIG. 1 can determine the amount of lung tissue of the lobe, segment, or sub-segment to be treated. In another embodiment, the amount of lung tissue can be determined external to the generator, such as by a physician or clinician.

At step 807, the method can include determining which lung(s), lobe(s), and/or segments of bronchi to treat based on the data gathered in step 806. A first method of determining what portion of the lungs to treat includes calculating a Tissue-to-Air ratio (TAR) for different lobes, segments, and/or sub-segments in a lung and using the TARs in treatment planning. The TAR value for a given lobe or segment is determined by dividing the mass or volume of tissue of the lobe or segment by the mass or volume of air within the lobe or segment, both of which were determined in step 806 above.

The TAR value(s) can be used for treatment planning as a factor in determining dose of vapor to administer, time of delivery, etc., as a tool to determine whether to include or exclude a patient from treatment, or it can be used to determine which segment(s) of the lung should be treated.

One exemplary method in which the TAR values can be used in treatment planning is by comparing the TAR of the superior lobes to the inferior lobes to determine if treating the superior lobe (or alternatively, if treating the inferior lobe) would effectively reduce total lung volume. The superior lobes are typically the lobes to which water vapor is delivered to damage the airway walls, so if the superior lobes have TAR values that are less than the inferior lobes, it may be an indication that treatment of the superior lobe will effectively reduce the volume of the lung. Table 1 is an example of calculated TAR values for a patient.

TABLE 1

Tissue-to-Air Ratio

| | TAR | | TAR |
|---|---|---|---|
| Left Lung | 10% | Right Lung | 10% |
| Superior Lobe | 9% | Superior Lobe | 9% |
| LB1 | 9% | RB1 | 9% |
| LB2 | 9% | RB2 | 8% |
| LB3 | 8% | RB3 | 10% |
| LB4 | 9% | Middle Lobe | 10% |
| LB5 | 10% | RB4 | 9% |
| Inferior Lobe | 11% | RB5 | 10% |
| LB6 | 9% | Inferior Lobe | 11% |
| LB7 | 9% | RB6 | 9% |
| LB8 | 10% | RB7 | 12% |
| LB9 | 10% | RB8 | 9% |
| LB10 | 12% | RB9 | 11% |
| | | RB10 | 14% |

In reference to Table 1, the TAR for the right superior lobe is 9% and TAR for the right inferior lobe is 11%, while the TAR for the left superior lobe is 9% and the TAR for the left inferior lobe is 11%. Calculating the TAR heterogeneity (i.e., the ratio of TARs between respective lobes in each lung) can give an indication as to whether one or both lungs should be treated. Generally, the higher the volume of air in a segment of the lung, the more likely there is residual volume and emphysema in that segment. Theoretically, if a segment of the lung has a larger percentage of air than a different segment at the same hierarchy level in the lung, the segment with the greater percentage of air would more greatly benefit from vapor treatment to collapse a portion of that segment. This, in turn, would theoretically result in a greater reduction in the volume of the lung.

In Table 1, the left superior lobe is approximately equally hyperinflated as the right superior lobe, which indicates that both superior lobes are good candidates for treatment, which could likely result in a reduction in volume of the right and left lung including an expansion of the better functioning inferior lobes (and the entire lung overall). However, if the upper and lower lobes were both relatively low or below a predetermined level, e.g., 4%, the treatment might not be as effective, or a decision may be made to exclude the patient from treatment. Table 2 is an example of TAR Heterogeneity values for the patient.

TABLE 2

| TAR Heterogeneity | | | |
|---|---|---|---|
| Left Inferior to Left Superior | 1.2 to 1 | Right Inferior to Right Superior | 1.2 to 1 |
| Left Lingual to Left Superior | 1.1 to 1 | Right Middle to Right Superior | 1.1 to 1 |

Referring to Table 2, the TAR heterogeneity is the difference in TAR ratio between the respective lobes. This value gives an indication of how advanced the disease is in the lungs, and can be used as another factor in determining which lung or which portion of the lung(s) to treat. Generally, the greater the difference or TAR heterogeneity, the more advanced the disease. In Table 2, the TAR heterogeneity values are approximately the same, which again indicates that both lungs may be good candidates for treatment. However, if the TAR heterogeneity of the right lung had been greater than the TAR heterogeneity of the left lung, then that could have been an indication that the right lung should be treated instead of the left lung. It should be understood though, that even if the TAR heterogeneity of the right lung had been greater than the TAR Heterogeneity of the left lung, both lungs can still be treated with vapor energy.

Another method of using TAR values for treatment planning is to compare the TAR for comparable right and left lung lobes (e.g., compare right superior lobe to left superior lobe). If a treatment involves only unilateral treatment (delivering vapor to only either the left or right lung), a determination could be made about which lung should be treated to more effectively reduce the volume of the lung. Theoretically, the lung with the lower TAR would be the more diseased lung and the patient would benefit from receiving treatment to that lung. Treatments however, may be done bilaterally as well.

Yet another factor in determining which lung(s), lobe(s), and/or segment(s) of the lung to treat with vapor energy can be determined by calculating perfusion of the lungs. Perfusion is a measurement of blood flow to the lungs and can be measured by techniques known in the art. Tables 3 and 4 give examples of perfusion and perfusion heterogeneity for the patient.

TABLE 3

| Perfusion | | | |
|---|---|---|---|
| Left Lung | 48% | Right Lung | 52% |
| Left Superior Field | 12% | Right Superior Field | 8% |
| Left Inferior Field | 14% | Right Inferior Field | 19% |

TABLE 4

| Perfusion Heterogeneity | | | |
|---|---|---|---|
| Left Inferior to Left Superior | 1.2 to 1 | Right inferior to Right Superior | 2.4 to 1 |

Tables 3 and 4 above indicate that the right superior lobe has less perfusion than the left superior lobe, and that the right superior lobe has larger tissue perfusion heterogeneity than the left superior lobe. The smaller amount of perfusion and larger perfusion heterogeneity ratio in the right superior lobe suggests that it is more diseased than the left lung. This data indicates that treatment could be more effective if the right superior lobe was treated, if the procedure were to be a unilateral treatment. However, as discussed above, the other data suggests that a bilateral treatment could also be effective.

Generally, treatment of segments in the lungs should be in the order of smallest to largest size to reduce the risk of over-dose. In one example, if the superior lobe of the left lung is to be treated, the order may be LB1, LB2, LB3 (or similarly, LB1+2, LB3). Similarly, if the superior lobe of the right lung is to be treated, the order may be RB1, RB2, RB3. Each of the segments should typically be treated completely unless treatment of the particular segment is not feasible. It should be understood that various patients have different anatomies, so the order of treatment will vary from patient to patient. Thus, the smallest to largest size lobe may not always be LB1, LB2, LB3, etc.

It should be noted that in the examples above, discussion focused on treatment of the superior lobes of the patient. This is because there are more patients with superior lobe diseases and the inferior lobes are typically more difficult to access. However, the same principles can be applied to treat the inferior lobes of the patient with similar results if the user or clinician determines that the inferior lobes should be treated. In one embodiment, the electronic controller in generator 12 of FIG. 1 can determine the TARs, the TAR Heterogeneity, the Perfusion, and the Perfusion Heterogeneity of lung tissue of the lobe, segment, or sub-segment to be treated. In another embodiment, these values can be determined external to the generator, such as by a physician or clinician.

At step 808, the method can further include determining an effective vapor dose to be delivered to the lobe, segment or sub-segment based. A safe and efficacious dose of energy (e.g., calories/gram) to be applied to the lung tissue must be determined depending on the desired degree of injury for the lung tissue. In general, as the dose increases the degree of injury to the tissue increases. Doses of vapor from about 5 cal/g to about 40 cal/g will generally result in coagulative necrosis with little, or even no, thermal fixation. In one embodiment, an ideal target vapor dose is approximately 10 cal/g. The degree of thermal fixation will generally increase as the dose increases above 40 cal/g. The desired degree of injury to the lung tissue can therefore be controlled by altering the dose of vapor applied to the tissue. In one embodiment, the electronic controller in generator 12 of FIG. 1 can determine the effective vapor dose to be delivered to the lobe, segment, or sub-segment to be treated. In another embodiment, the effective vapor dose can be determined external to the generator, such as by a physician or clinician.

To cause necrosis, the energy dose in some embodiments varies from about 5 cal/g to about 40 cal/g. These limits are, however, not intended to be definitive limitations of the doses applied, as other delivery parameters described below (e.g., delivery rate, delivery duration, etc.) may allow different doses to be applied to accomplish the same or similar injury to the tissue.

At step 810, the amount of total energy that needs to be applied by the delivery system to the tissue can be determined. This is generally accomplished by multiplying the dose from step 808 by the amount of tissue to be treated from step 806 to determine the total amount of energy to deliver. For example, the dose, in calories per gram, multiplied by the amount of tissue, in grams, will result in the total amount of calories to be delivered to the target tissue. In one embodiment, the electronic controller in generator 12 of FIG. 1 can determine the amount of total energy that needs to be applied by the delivery system to the lobe, segment, or sub-segment to be treated. In another embodiment, the amount of total energy that needs to be applied by the delivery system can be determined external to the generator, such as by a physician or clinician.

At step 812, the flow rate of the delivery system can be determined. The flow rate is generally between about 20 cals/second to about 200 cals/second. In one embodiment, the flow rate is 40 call/second. Again, these limitations are not intended to be definitive limitations and the delivery rate may be higher or lower depending on other treatment and/or delivery parameters. In one embodiment, the electronic controller in generator 12 of FIG. 1 can determine the flow rate of the delivery system. In another embodiment, the flow rate of the delivery system can be determined external to the generator, such as by a physician or clinician.

At step 814, the method can further include determining the treatment duration for delivering the vapor to the lungs. The treatment duration can be calculated by dividing the total amount of energy to be delivered from step 810 (calories) by the energy flow rate from step 812 (calories per second). For example, to deliver 300 calories to a segment of the lung at a flow rate of 30 cals/second, the treatment duration would be 10 seconds. Treatment duration is typically between 3 and 10 seconds. Treatment duration longer than 10 seconds is not recommended for safety reasons, and treatment duration less than 3 seconds is typically not effective. In one embodiment, the electronic controller in generator 12 of FIG. 1 can determine the treatment duration for delivering the vapor to the lungs. In another embodiment, the treatment duration for delivering the vapor to the lungs can be determined external to the generator, such as by a physician or clinician.

At step 816, the delivery parameters can be set on the delivery system, such as flow rate from step 812 and treatment duration from step 814. These parameters can typically be set via controls on a delivery system, such as on the user interface in FIG. 4. Once the user sets the flow rate, the generator can establish the requisite amount of pressure in the generator to deliver the vapor at the desired flow rate by adjusting the amount of heat applied in the generator. Changing the flow rate setting can cause the generator to adjust the amount of pressure in the generator. The pressure in the vapor generator can range from between about 10 psi (69 kPa) to over about 100 psi (689 kPa), for example. In another embodiment, the delivery parameters do not need to be manually set by a user, but instead can be automatically set by an electronic controller in the generator, for example.

Treatment times can vary depending on the volume, mass to be treated, and the desired injury to the tissue. Treatment times can vary from about 2 seconds to about 30 seconds. In some embodiments for causing necrosis to reduce the volume of the lung, the safe and effective treatment time is between about 4 and about 10 seconds. To thermally fix the lung, for example, the treatment time may be longer in order to injure the tissue to a greater degree.

At step 818, the vapor can be administered to the lungs of the patient at the set parameters.

FIGS. 9-13 are illustrations showing administration of vapor (e.g., administration of vapor at step 818) to the various segments of bronchi in the lungs of a patient, such as the patient having the TAR, TAR heterogeneity, and perfusion data described above with respect to flowchart 800. During treatment, it is typically desirable to treat as far down each branch as possible, to deliver a dose into the smallest possible branch that can be used within the dosage parameter limits. Thus, treatment at the sub-sub-segment level is the most desirable, followed by treatment at the sub-segment level and finally treatment at the segment level.

Figure 9A:
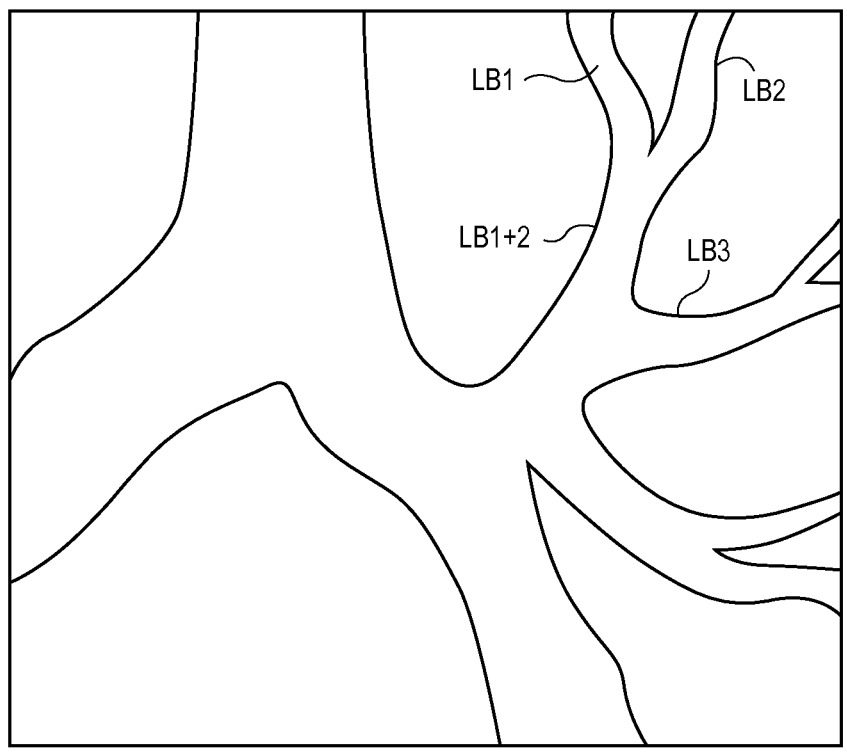
Figure 9B:
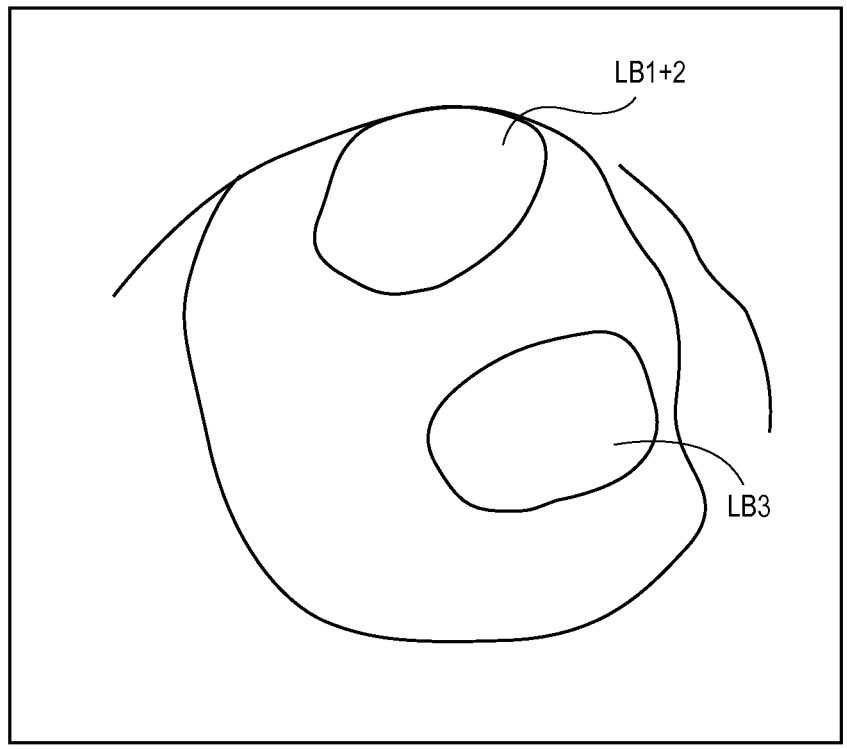

FIG. 9a is a schematic drawing of the LB1, LB2, and LB3 segments of the left superior lobe of the patient described above. For this particular patient, the LB1 and LB2 segments combine to form a LB1+2 segment. Some patients have combined segments, such as the LB1+2, and some patients do not. While the example described with reference to FIG. 9a includes a LB1+2 segment, it should be understood that the segmental anatomy of other patients may be different. FIG. 9b is a cross sectional drawing of the LB1, LB2, and LB3 segments of the left superior lobe of the patient, and shows a view of the LB1, LB2, and LB3 segments from within the bronchi. The relative locations of the segmental bronchi and the cross sectional areas of each of the segments LB 1+2, and LB3 of the patient can be visualized by the clinician by referring to FIGS. 9a-9b.

FIG. 9c illustrates a treatment plan and or treatment guide to be used by a clinician during administration of vapor to the LB1 and LB2 segments, or apicoposterior LB 1+2 segment of the left superior lobe of the patient. The drawings shown in FIGS. 9a-9b, and the treatment guide illustrated in FIG. 9c, can be displayed on a monitor or user interface of the delivery system for use by the clinician or physician during treatment. In another embodiment, the information shown in FIGS. 9a-9c can be a workup or chart calculated based on the imaging and calculated data described above (i.e., tissue volume/mass, TAR, perfusion, etc).

FIG. 9D indicates the segment volume 902, segment mass 904, percent of the superior lobe 906, TAR 908, and perfusion 910 of the apicoposterior segment LB1+2. The segment volume, mass, and percent of the lobe can be determined as described above, such as by imaging the lungs and extracting and/or calculating the parameters with software or other algorithms in step 806 of FIG. 8, for example. The TAR and perfusion can be calculated as described above, in step 807 of FIG. 8, for example.

FIG. 9E indicates the target vapor dose 912, the vapor dose lower limit 914, the vapor dose upper limit 916, and the flow setting or flow rate 918. The target vapor dose or flow rate can be determined by the clinician as described above in step 808 of FIG. 8. In the example shown in FIG. 9E, the target vapor dose has been selected to be 10 calories per gram and the flow setting of 6 corresponds to a flow rate of 40 calories per second. The upper and lower vapor dose limits are typically chosen based on the desired type of injury to be administered to the lungs and other health considerations. In this example, the lower dose limit is set to 7.5 calories per gram and the upper dose limit is set to 10 calories per gram. The flow setting is an indicator to the clinician or physician on what setting to use on the delivery system to achieve the desired target vapor dose.

FIG. 9c also includes a schematic illustration of the LB1+2 segment, as well as the sub-segments 920 and sub-sub-segments 922 distal to the LB1+2 segment. FIGS. 9F, 9G, and 9H indicate the treatment time 923 in seconds and the vapor dose 924 in calories per gram that it would take to deliver the total amount of energy calculated in step 810 of FIG. 8 above. Since the segment mass is 38 grams and the target vapor dose is 10 calories per gram, the total amount of energy to deliver to the LB1+2 segment is 380 calories. Dividing 380 calories by the flow rate of 40 calories per second results in a treatment time of 9.5 seconds at an actual dose of 10 calories per gram to treat at the LB1+2 at the segment level.

It can be seen in FIGS. 9G and 9H that treatment at the sub-segment and sub-sub-segment levels are not recommended in this example (DNT or "Do Not Treat"). This is due to the calculated treatment times for the sub-segment and sub-sub-segment levels being outside of the desired range of treatment durations. This range of desired treatment durations is typically between 3-10 seconds. Icons 926, 928, and 930 positioned next to FIG. 9G are to be used by the physician to determine treatment time if treatment is possible at the sub-segment or sub-sub-segment level. These icons will be discussed in more detail below.

Figure 10A:
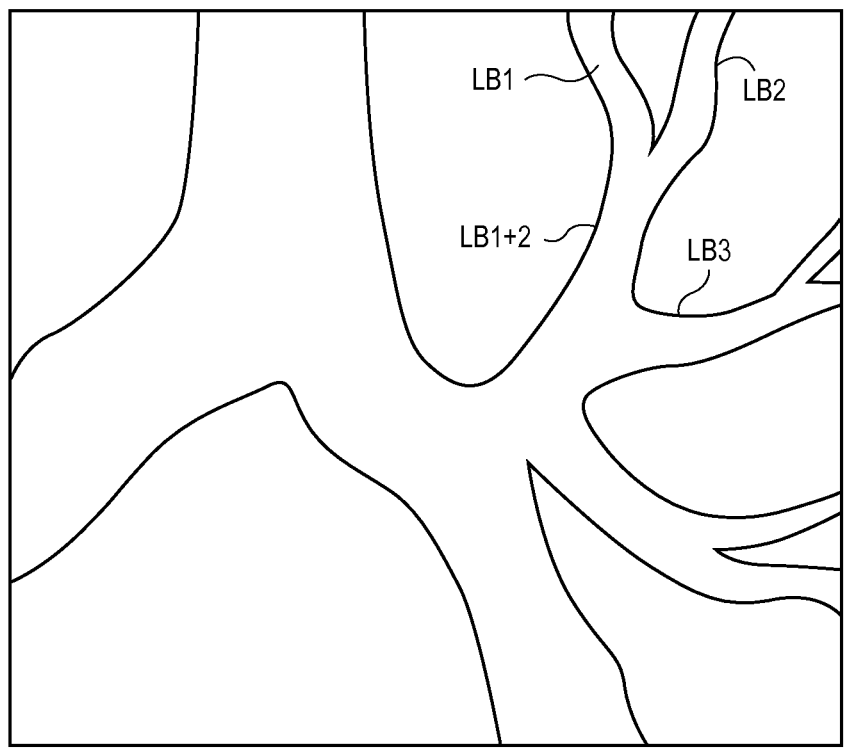
Figure 10B:
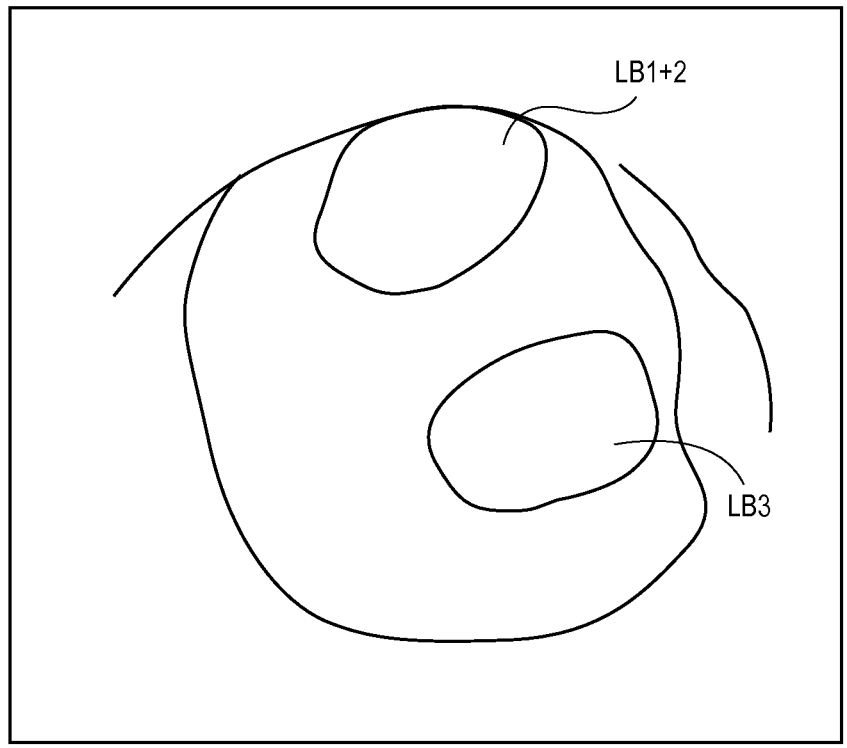

FIG. 10a is a schematic drawing of the LB1, LB2, and LB3 segments of the left superior lobe. FIG. 10b is a cross sectional drawing of the LB1, LB2, and LB3 segments of the left superior lobe, and shows a view of the LB1, LB2, and LB3 segments from within the bronchi.

FIG. 10c illustrates a treatment plan and or treatment guide to be used by a clinician during administration of vapor to the LB3 segment of the left superior lobe. Treatment of the LB3 segment can be accomplished by following the same principles discussed above with respect to FIGS. 9a-9c.

In FIG. 10c, an LB3 mass of 43 g and a target vapor dose of 10 calories per gram results in a total energy of 430 calories to be delivered to the segment. However, at a flow rate of 40 calories per second and a maximum treatment time of 10 seconds, the maximum dose that can be delivered to the segment at the LB3 segment level is a dose of 9.4 calories per gram, as shown in FIG. 10F. Since this can be a sub-optimal dose, the physician can consider treating the LB3 segment at the sub-segment or sub-sub-segment level to use an optimal dose (i.e., 10 calories per gram).

FIGS. 10G and 10H indicate the treatment times 923 and vapor doses 924 for treatment of LB3 at the sub-segment and sub-sub-segment level. FIG. 10G contains three rows of treatment times and doses, each row corresponding to an icon, such as icons 926, 928, and 930. The icons are to be used by the physician to determine which treatment times to use at each of the respective sub-segments. To determine which treatment time to use in this example, the physician can advance the delivery system within the lungs into the LB3 segment until reaching the sub-segmental level, which branches into two sub-segments as illustrated by the schematic drawing in FIG. 10c.

Once the physician has positioned the catheter or bronchoscope at the sub-segmental level, the physician can observe the relative cross sectional areas of the two sub-segments. If the sub-segments are approximately the same size, as shown in icon 926, then the treatment times and doses from the first row in FIG. 10G should be used. If the sub-segments are approximately at a ratio of 1 to 2 to each other, or 33% to 66%, as shown in icon 928, then the treatment times and doses from the second row in FIG. 10G should be used. Similarly, if the sub-segments are approximately at a ratio of 1 to 3 to each other, or 25% to 75%, as shown in icon 930, then the treatment times and doses from the third row in FIG. 10G should be used.

If the physician wishes to treat at the sub-sub-segment level, then approximating the relative sizes of the sub-sub-segments is not necessary, and each sub-sub-segment can be treated with the same dose and treatment time, as shown in FIG. 10H.

Typically the physician or clinician will have to make judgment calls on whether to treat at the segmental level, the sub-segmental level, or the sub-sub-segmental level. These decisions will typically be made once the physician has inspected the tissue to be treated, such as with a catheter or bronchoscope. Upon viewing the tissue to be treated, the physician may determine that an airway is blocked or occluded, or may see that the tissue does not have enough lumen length to deploy an occlusion balloon from the catheter tip to block off the airways. Thus while treatment may be desired at the sub-sub-segment level, it may not always be possible to actually treat at that level and treatment at the segment or sub-segment levels should be considered by the physician.

Figure 11A:
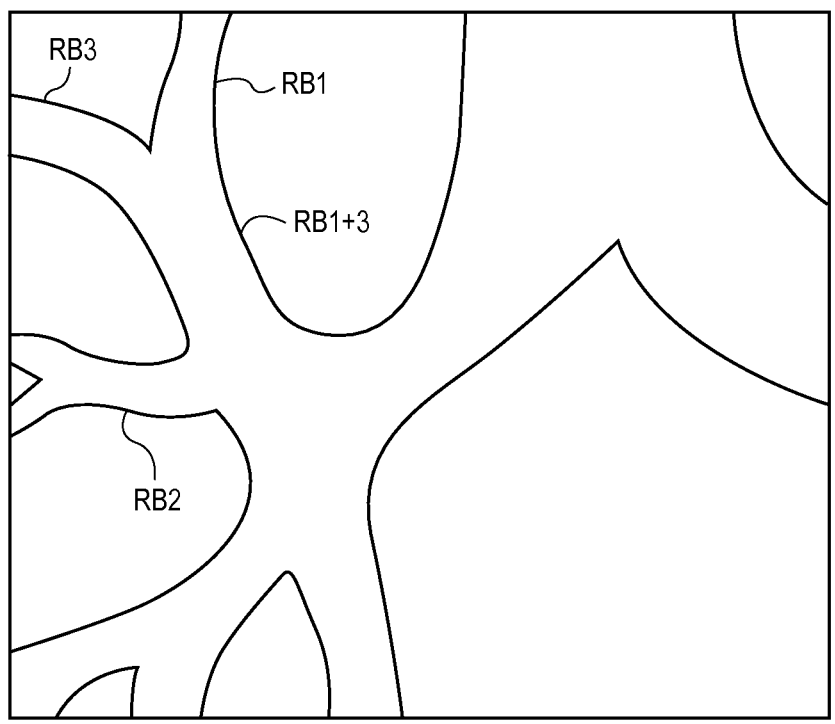
Figure 11B:
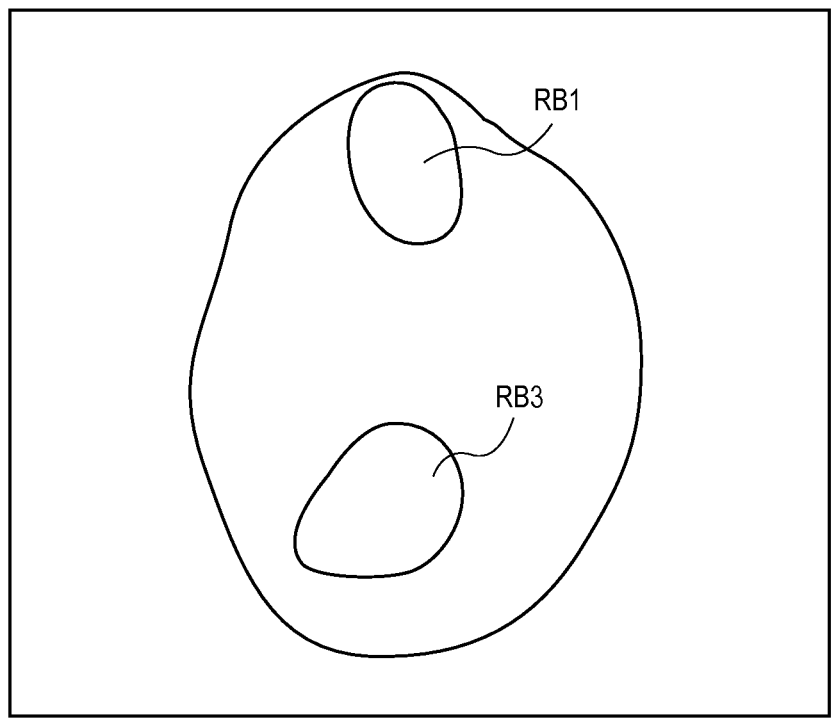
Figure 12A:
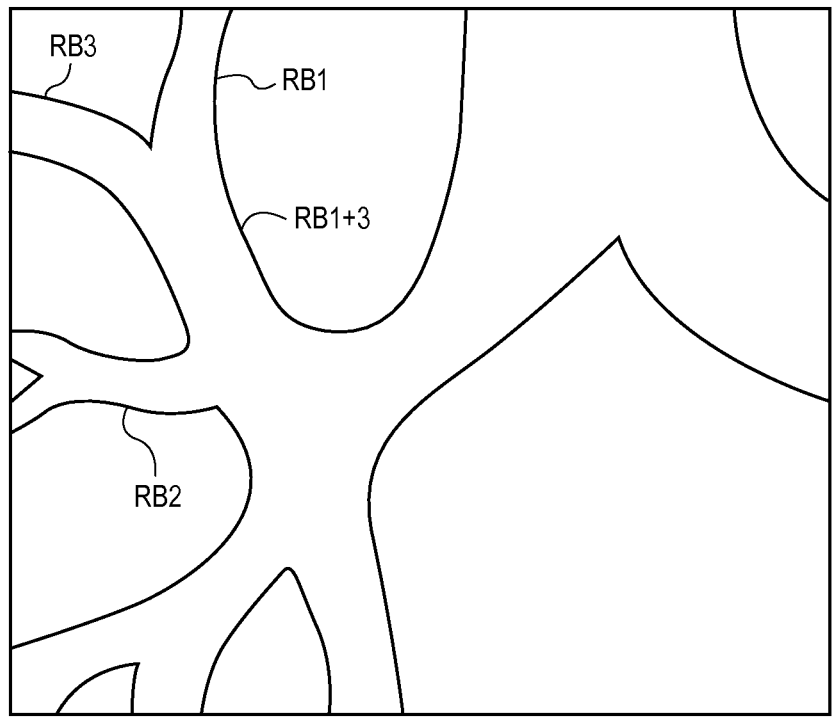
Figure 12B:
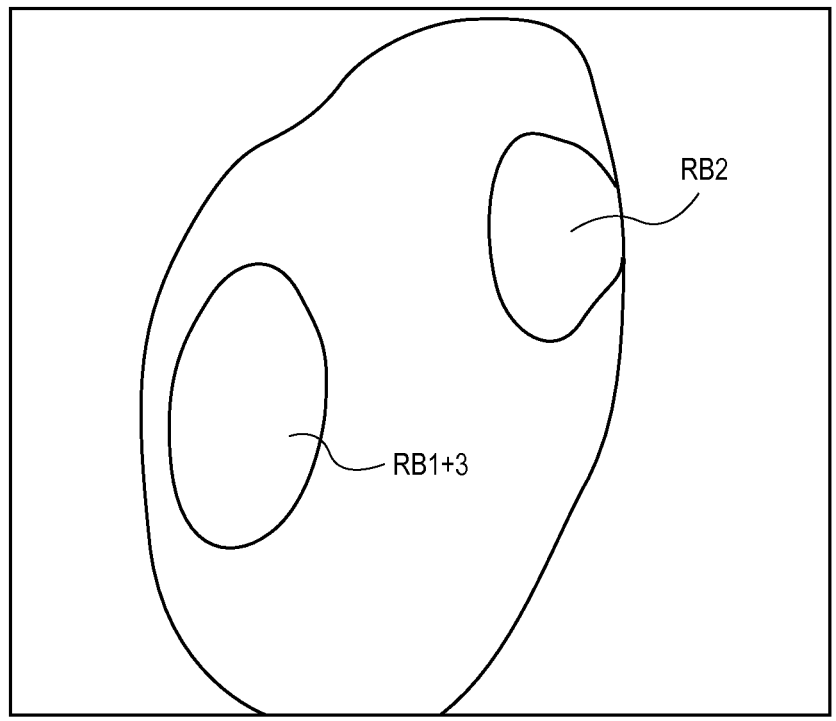
Figure 13A:
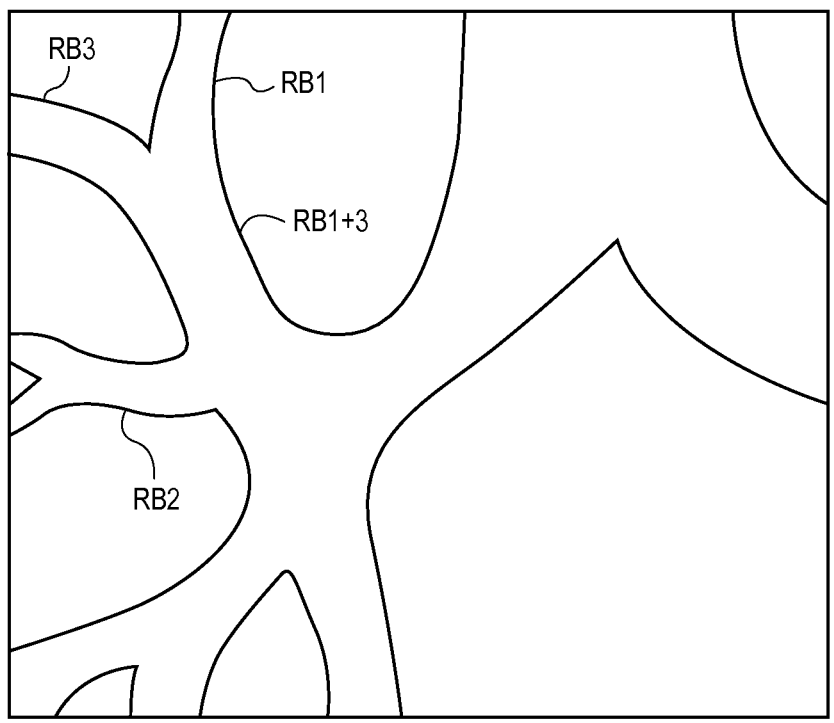
Figure 13B:
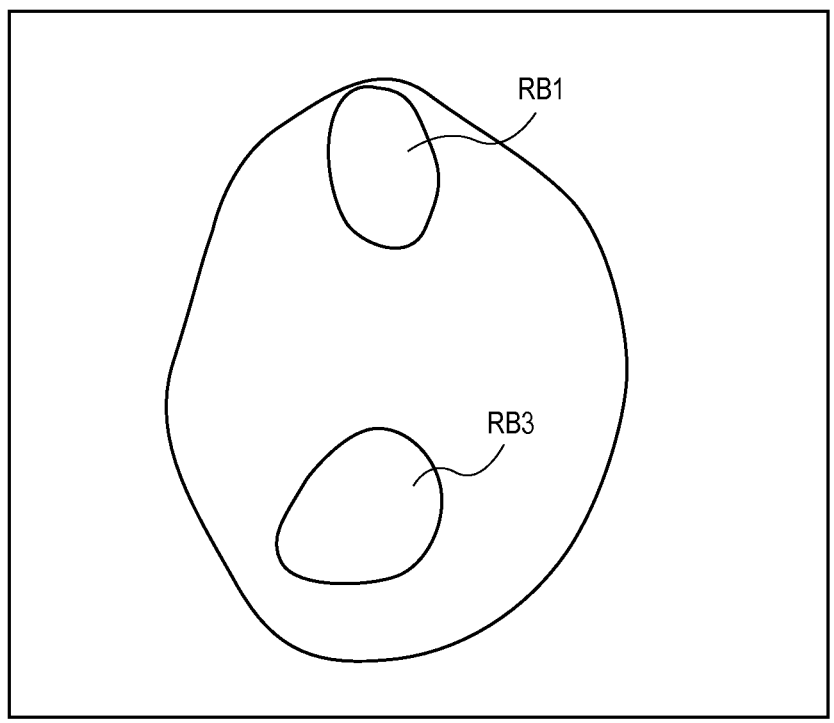

FIGS. 11-13 illustrate treatment plans and treatment guides for treating the right superior lobe in this example, including the RB1, RB2, and RB3 segments. The principles discussed above in FIGS. 9-10 to determine treatment doses, treatment times, and treatment locations can be applied to FIGS. 11-13 for treatment of the right superior lobe.

An additional factor in treatment planning is using a 3D airway reconstruction to determine if any anomalies exist in the patient's lung that would effect vapor treatment. For example, if a 3D airway reconstruction shows a collapsed portion of the lung, it can be an indication that vapor treatment would have little effect on that segment. It can be therefore be determined that administering vapor to the collapsed segment with the collapsed airway would not be feasible due to the inability of the catheter to enter the region and/or would have little effect to reduce the volume of the lung and that the vapor should be delivered to a different segment(s) in the lung.

The treatment planning described above can be used to generate patient-specific treatments. 3D reconstruction models, TAR values, and percent of air in a segment will vary from patient to patient. Being able to analyze these tools, either qualitatively or quantitatively, can assist in determining the best course of treatment to delivery vapor to the patient to reduce the volume of the lung. Additionally, these factors can be used as exclusionary tools to determine if a patient should or should not be a recipient of such treatment.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for determining treatment parameters and applying energy to lung tissue with vapor to selectively injure the tissue, the system comprising:
   a vapor generator adapted to generate a vapor from a liquid;
   a delivery catheter coupled to the vapor generator; and
   an electronic controller configured to determine an amount of energy to be delivered by the vapor to a lung segment to be treated based on a mass of the segment to be treated and a dosage, the controller also configured to determine a duration for delivering the vapor based on the amount of energy to be delivered and an energy flow rate of the vapor generator.

2. The system of claim 1 wherein the delivery catheter comprises a balloon adapted to seal an airway.

3. The system of claim 1 wherein the delivery catheter comprises a shaft adapted to be delivered to a patient's lung through a bronchoscope.

4. The system of claim 1 further comprising a control to adjust delivery time of vapor from the vapor generator based on a duration determined by the electronic controller.

5. The system of claim 1 further comprising a control to adjust the energy flow rate of the vapor generator.

6. A system for determining treatment parameters and applying energy to lung tissue with vapor to selectively injure the tissue, the system comprising:

a vapor generator adapted to generate a vapor from a liquid;
a delivery catheter coupled to the vapor generator; and
an electronic controller configured to determine an amount of energy to be delivered by the vapor to a lung segment to be treated based on a mass of the segment to be treated and a dosage, the controller also configured to determine a duration for delivering the vapor based on the amount of energy to be delivered and an energy flow rate of the vapor generator, wherein the energy flow rate of the vapor generator is between 20 calories/second and 200 calories/second.

7. The system of claim 6 wherein the delivery catheter comprises a balloon adapted to seal an airway.

8. The system of claim 6 wherein the delivery catheter comprises a shaft adapted to be delivered to a patient's lung through a bronchoscope.

9. The system of claim 6 further comprising a control to adjust delivery time of vapor from the vapor generator based on a duration determined by the electronic controller.

10. The system of claim 6 further comprising a control to adjust the energy flow rate of the vapor generator.

* * * * *